United States Patent
Colter et al.

(10) Patent No.: US 8,889,413 B2
(45) Date of Patent: Nov. 18, 2014

(54) MAMMARY ARTERY DERIVED CELLS AND METHODS OF USE IN TISSUE REPAIR AND REGENERATION

(71) Applicant: DePuy Synthes Products, LLC, Raynham, MA (US)

(72) Inventors: David C. Colter, Hamilton, NJ (US); Charito Buensuceso, North Brunswick, NJ (US); Christian C. Kazanecki, Martins Creek, PA (US); Anna Gosiewska, Skillman, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/792,461

(22) Filed: Mar. 11, 2013

(65) Prior Publication Data

US 2013/0183756 A1    Jul. 18, 2013

Related U.S. Application Data

(60) Continuation-in-part of application No. 13/671,720, filed on Nov. 8, 2012, which is a division of application No. 12/885,855, filed on Sep. 20, 2010, now Pat. No. 8,323,972.

(60) Provisional application No. 61/247,228, filed on Sep. 30, 2009.

(51) Int. Cl.
C12N 5/00    (2006.01)
C12N 5/02    (2006.01)
C12N 5/071    (2010.01)
C12N 5/0775    (2010.01)

(52) U.S. Cl.
CPC ............ *C12N 5/069* (2013.01); *C12N 2533/40* (2013.01); *C12N 5/0692* (2013.01); *C12N 5/0668* (2013.01); *C12N 2509/00* (2013.01)
USPC ........................................................ 435/381

(58) Field of Classification Search
None
See application file for complete search history.

(56) References Cited

U.S. PATENT DOCUMENTS

| | | | |
|---|---|---|---|
| 5,286,632 A | 2/1994 | Jones |
| 5,320,962 A | 6/1994 | Stiles |
| 5,342,761 A | 8/1994 | MacLeod |
| 6,638,768 B1 | 10/2003 | Le Mouellic |

(Continued)

FOREIGN PATENT DOCUMENTS

| WO | WO 90/11354 | 10/1990 |
|---|---|---|
| WO | WO 92/03917 | 3/1992 |

(Continued)

OTHER PUBLICATIONS

Sachlos et al., Making Tissue Engineering Scaffolds Work. Review on the Application of Solid Freeform Fabrication Technology to the Production of Tissue Engineering Scaffolds, European cell and materials, vol. 5. 2003 (pp. 29-40).*

(Continued)

*Primary Examiner* — Catherine Hibbert
*Assistant Examiner* — Reza Ghafoorian

(57) ABSTRACT

An isolated mammalian internal mammary artery-derived cell is disclosed. Furthermore, methods of isolating the mammalian internal mammary artery-derived cell are disclosed. The cell is useful in tissue engineering technologies, specifically in vascular tissue engineering.

5 Claims, 11 Drawing Sheets

(56) References Cited

U.S. PATENT DOCUMENTS

| | | |
|---|---|---|
| 8,323,972 B2 | 12/2012 | Colter et al. |
| 2009/0124007 A1 | 5/2009 | Cho |
| 2009/0275129 A1 | 11/2009 | Cooper et al. |

FOREIGN PATENT DOCUMENTS

| | | |
|---|---|---|
| WO | WO 93/04169 | 3/1993 |
| WO | WO 95/17911 | 7/1995 |
| WO | WO 2004019767 A2 | 3/2004 |
| WO | WO 2006012404 A1 | 2/2006 |

OTHER PUBLICATIONS

Stenn et al. Dispase, a neutral protease from *Bacillus polymyxa*, is a powerful fibronectinase and type IV collagenase, The Journal of Investigative Dermatology, vol. 93, No. 2 Aug. 1989.*

Tintut et al. Multilineage Potential of Cells from the Artery Wall. *Circulation* 2505-2510, (2003).

Zengin et al. Vascular wall resident progenitor cells: a source for postnatal vasculogenesis. *Development* 133, 1543-1551 (2006).

Pasquinelli Gianandrea et al., Thoracic aortas from multiorgan donors are suitable for obtaining resident angiogenic mesenchymal stromal cells, Stem Cells, Jul. 7, 2007, 1627-1634, vol. 25.

Pasquinelli Gianandrea et al., Supplemental: Thoracic aortas from multiorgan donors are suitable for obtaining resident angiogenic mesenchymal stromal cells, Stem Cells, Jul. 2007, 1-7.

Phinney Donald G. et al., Concise review: Mesenchymal stem/multipotent stromal cells: The state of transdifferentiation and modes of tissue repair-Current views, Stem Cells, Nov. 2007, 2896-2902, vol. 25, No. 11.

Mohler, E.R. 3$^{rd}$ et al., Identification and characterization of calcifying valve cells from human and canine aortic valves, The Journal of Heart Valve Disease, May 1999, 254-260, vol. 8, No. 3.

Abedin Moeen et al., Mesenchymal stem cells and the artery wall, Circulation Research, Oct. 1, 2004, 671-676, vol. 95, No. 7.

Dominici M et al., Minimal criteria for defining multipotent mesenchymal stromal cells, The International Society for Cellular Therapy position statement, Cytotherapy, Aug. 1, 2006, 315-317, vol. 8, No. 4.

Pasquinelli Gianandrea et al., Multidistrict human mesenchymal vascular cells: pluripotency and stemness characteristics, Cytotherapy, May 2010, 275-287, vol. 12, No. 3.

Merriam-Webster Inc., Webster's Ninth New Collegiate Dictionary, "Entire" 1990, p. 415.

Moss et al., Isolation of Endothelial Cells and Vascular Smooth Muscle Cells from Internal Mammary Artery Tissue, The Ochsner Journal: Oct. 2007, vol. 7, No. 3, pp. 133-136.

Pasquinelli et al., Smooth muscle cell injury after cryopreservation of human thoracic aortas, Cryobiology 52 (2006) 309-316.

Stenn et al. Dispase, Neutral protease from *Bacillus polymyxa*, is a powerful fibronectinase and type IV collagenase, The Jounal of Investigative Dermatology, vol. 93, No. 2 (Aug. 1989) 287-290.

* cited by examiner

IMAC-seeded TEBV grafts after 3 days of cell culture and 3 hours at RT mock-ship.

IMAC-seeded TEBV grafts after 3 days of cell culture, 3 hours at RT mock-ship and overnight in cell culture incubator.

MAMMARY ARTERY DERIVED CELLS AND METHODS OF USE IN TISSUE REPAIR AND REGENERATION

RELATED APPLICATIONS

This is a continuation-in-part application of U.S. application Ser. No. 13/671,720, filed Nov. 8, 2012, which is a divisional application of U.S. patent application Ser. No. 12/885,855, filed Sep. 20, 2010, which is a non provisional application of U.S. patent application Ser. No. 61/247,228, filed Sep. 30, 2009, which is incorporated by reference.

FIELD OF THE INVENTION

The invention generally relates to mammalian mammary artery-derived cells isolated from mammalian internal mammary arteries. The invention further relates to methods for the isolation of the mammalian internal mammary artery-derived cells. Combining the isolated internal mammary artery-derived cells with a scaffold provides methods for use in a tissue-engineered device.

BACKGROUND OF THE INVENTION

The internal mammary artery, also known as the internal thoracic artery, perfuses the anterior chest wall and mammary glands. The internal mammary artery has a superior, long-term patency compared to saphenous vein grafts, and is regarded as the primary vessel of choice for cornonary artery bypass grafting. Compared to coronary and carotid arteries, the mammary artery is highly resistant to arthrosclerosis. This long-term resistance of the internal mammary artery to graft atherosclerosis, compared with the saphenous vein has been attributed, at least in part, to its superior endothelial cell function. In addition, the response of the internal mammary artery to mechanical injury is also different from that of coronary arteries. Human coronary arteries respond to balloon angioplasty by promoting cell migration and proliferation, leading to the formation of neointima and restenosis in approximately 40% of cases. However, unlike coronary arteries and saphenous vein graft, restenosis was not found in internal mammary artery grafts after percutaneous transluminal angioplasty. Therefore, the internal mammary artery could be a valuable tissue source for vascular progenitor cells.

It has been well documented that ectopic tissue, composed of cartilage, bone, and fat, is able to form within the wall of arteries. This phenomenon is termed metaplasia and suggests that multipotential progenitor cells may reside within the arterial wall. Osteogenic and chondrogenic differentiation within the artery wall is recognized clinically as vascular calcification and this type of mineralization is associated with increased cardiovascular injury. Vascular calcification is known to increase aortic stiffness, resulting in systolic hypertension, coronary insufficiency, left ventricular hypertrophy, ischemia, and congestive heart failure. In fact, approximately 85% of plaques causing coronary thrombosis are calcified. It has been suggested that progenitor cells within the artery wall might play a role in plaque formation, calcification and arthrosclerosis. Therefore understanding how these cells contribute to vascular pathology, as well as repair might lead to improved therapies for cardiovascular indications.

Many laboratories are currently focused on understanding the role of stem cells in vascular physiology. It has been shown that adult organs contain stem cells that are involved in organ maintenance and repair after injury. Therefore, it is feasible that adult progenitor cells can be isolated from many, if not all types of organ tissue. These tissue-specific progenitor cells could then be exploited for tissue-specific therapeutic purposes.

Zingin et al., recently demonstrated the existence of a 'vasculogenic zone' in the adult human vascular wall. In this study, putative progenitor cells were isolated from human internal thoracic arteries. To harvest the cells, arteries were minced and digested with trypsin/EDTA at 37° C. for 5 minutes. Non-digested tissues were removed by filtration. The suspension was centrifuged and the resulting cell pellet was resuspended into endothelial growth culture medium and plated onto collagen or fibronectin-coated dishes. These cells demonstrated the expression of CD34. Progenitor cells, expressing KDR/Flk1 and CD45 were also shown to be present within the vascular wall of the internal mammary artery. These data suggest that there is a pool of progenitor cells within the wall of the internal mammary artery.

The identification and isolation of a vascular wall progenitor cell that is manufacturable and resistant to atherosclerosis might prove to be beneficial for cell therapy and tissue engineering applications. In an attempt to harness the internal mammary artery's unique anti-atherogenic and mechanical attributes, we have isolated and characterized unique progenitor cells from human internal mammary arteries and evaluated their utility in tissue engineering applications.

SUMMARY OF THE INVENTION

We disclose mammalian internal mammary artery-derived cells isolated from mammalian internal mammary arteries. Methods for the isolation of the mammalian internal mammary artery-derived cells are also provided. Mammalian internal mammary artery-derived cells were characterized for cell morphology, growth potential, surface marker phenotype, secreted proteins, gene expression, multipotential differentiation and in vivo pro-angiogenic activity. These cells have utility for both cell and tissue engineering applications.

DETAILED DESCRIPTION OF THE INVENTION

Figure 1:
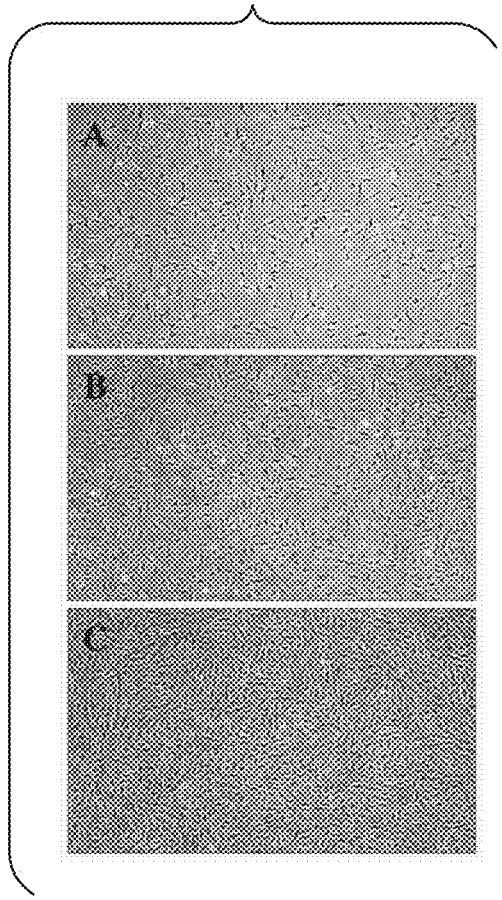
FIG. 1: Morphology. iMACs (internal mammary artery-derived cells) were cultured on collagen coated tissue culture flasks and phase-contrast images were obtained at passage 2 (A), passage 7 (B) and passage 23 (C). Cells show a homogeneous, fibroblastic morphology.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Cells of the invention" refer to a mammalian internal mammary artery-derived cell. "Differentiation" is the process by which an unspecialized ("uncommitted") or less specialized cell acquires the features of a specialized cell, such as a vascular cell, for example. A "differentiated or differentiation-induced cell" is one that has taken on a more specialized ("committed") position within the lineage of a cell. The term "committed," when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. A "lineage-specific marker" refers to a characteristic specifically associated with the phenotype of cells of a lineage of interest and can be used to assess the differentiation of an uncommitted cell to the lineage of interest.

"Internal mammary artery-derived cells" as used herein are cells isolated from a mammalian internal mammary artery. Internal mammary artery-derived cells can give rise to cells, such as adipocytes, or can give rise to one or more types of tissue, for example, vascular tissue, in addition to producing daughter cells of equivalent potential. These cells are "isolated" from the internal mammary artery, which refers to the separation of the cells from the surrounding tissue by enzymatic digestion. "Digested material" refers to the cells and tissue that are isolated from the mammalian internal mammary artery after being treated with an enzyme solution. This digested material is either discarded or directly plated onto tissue culture vessels. Cells that are contained within the "digested material" can attach to the tissue culture vessel and can be propagate in culture.

A "conditioned medium" is a medium in which a specific cell or population of cells has been cultured, and then removed. While the cells are cultured in the medium, they secrete cellular factors that can provide trophic support to other cells. Such cellular factors include, but are not limited to hormones, cytokines, extracellular matrix (ECM), proteins, antibodies, and granules. The medium containing the cellular factors is the conditioned medium.

Generally, a "trophic factor" is defined as a substance that promotes survival, growth, proliferation, maturation, differentiation, and/or maintenance of a cell, or stimulates increased activity of a cell. "Trophic support" is used herein to refer to the ability to promote survival, growth, proliferation, maturation, differentiation, and/or maintenance of a cell, or to stimulate increased activity of a cell. The mammalian internal mammary artery-derived cell of the invention produces trophic factors, including but not limited to, growth factors, cytokines, and differentiation factors. "Gene expression" refers to transcription of a gene into an RNA product, and optionally to translation into one or more polypeptide sequences.

In one embodiment, an isolated mammalian internal mammary artery-derived cell is provided. The cell is capable of self-renewal and expansion in culture wherein the cell is positive for the expression of each one of cell-surface markers CD29, CD44, CD73, CD166 and HLA-1, and negative for each one of cell-surface markers CD10, CD15, CD23, CD24, CD31, CD34, CD45, CD62p, CD80, CD86, CD104, CD117, CD133, CD138, CD141, CD146, VE-Cadherin, KDR/Flk-1 and HLA-2.

In another embodiment, the mammalian internal mammary artery-derived cell is positive for the expression of cell-surface marker HLA-1 and negative for expression of each one of cell-surface markers CD 10, CD31, CD34, CD45, CD133, CD141 and KDR/Flk-1.

In yet another embodiment, the mammalian internal mammary artery-derived cell is additionally positive for expression of CD29, CD44, CD73, CD166, and additionally negative for CD15, CD23, CD24, CD62p, CD80, CD86, CD104, CD117, CD138, CD146, VE-Cadherin, and HLA-2.

In another embodiment, the mammalian internal mammary artery-derived cell may secrete the trophic factors $\beta 2$ microglobulin, creatine kinase-MB, ENA-78, endothelin-1, eotaxin, fatty acid binding protein, ferritin, basic FGF, interleukin-6, interleukin-8, insulin, MCP-1, PAI-1, stem cell factor, TIMP-1, VCAM-1 and VEGF. The cell does not secrete Von Willebrand Factor or PDGF-bb.

In yet another embodiment, an isolated mammalian internal mammary artery-derived cell is provided, said cell capable of self-renewal and expansion in culture, wherein the cell is positive for gene expression of CD13, chemokine ligand 2, Ephrin A2, Ephrin A3, Endoglin, Endothelial PAS domain protein 1, Fibroblast growth factor-2, Fibroblast growth factor receptor-3, Hypoxia-inducible factor-1, Matrix metalenoprotinase-2, Neuropilin-1, Placental growth factor, Urokinase, Thrombospondin-2, TIMP inhibitor-1, TIMP inhibitor-3, TNF-12a, Troponin T type-1, VEGF-B and VEGF-C, tripartite motif-containing 33 (TRIM33), SRY (sex determining region Y)-box 11 (SOX-11), Notch homolog 2 (Drosophila) (NOTCH-2), cysteine rich transmembrane BMP regulator 1 (CRIM-1), homeobox D9 (HOXD9) and POU class 3 homeobox 3 (POU3F3).

In one embodiment, we provide a method for isolating a mammalian internal mammary artery-derived cell. This method comprises obtaining internal mammary artery tissue, digesting the artery sequentially in two steps to obtain digested material, isolating the cells from the digested material, and culturing the cells in growth media to provide the internal mammary artery-derived cells. The first digestion step comprises incubating the tissue in the presence of a metalloprotease, a neutral protease, and/or a mucolytic enzyme for a sufficient amount of time to partially digest the artery thereby removing the external debris and intimal layer of the artery. Suitable enzymes include, but are not limited to collagenase, dispase and hyaluronidase and combinations thereof In one embodiment, the artery is digested in collagenase and dispase. In one embodiment, the artery is incubated in the enzyme mixture in the first digestion step for about 60 minutes. The partially digested artery is then removed from the enzyme mixture and in a second digestion step placed into a fresh enzyme mixture for a sufficient amount of time to obtain the digested material containing the internal mammary artery-derived cells. In one embodiment, the artery is incubated in the enzyme mixture in the second digestion step for about 30 minutes to about 60 minutes. In another embodiment, the artery is incubated in the enzyme mixture in the second digestion step for about 60 minutes. The cells isolated from the digested material are then plated onto a collagen coated tissue culture vessel and cultured under standard conditions in growth medium. After a brief culture period, the cell is characterized for morphology, surface marker expression, gene expression, trophic factor secretion and multipotential differentiation.

In another embodiment, we provide a method of diagnostic and prognostic evaluation as well as for drug discovery for cardiovascular disease which uses mammalian internal mammary artery-derived cells to characterize cellular responses to biologic or pharmacologic agents involving isolating mammalian internal mammary artery-derived cells from a statistically significant population of individuals, culture expanding the mammalian internal mammary artery-derived cells from the statistically significant population of individuals to establish a plurality of cell cultures of mammalian internal mammary artery-derived cells, contacting the mammalian internal mammary artery-derived cell cultures with one or more biologic or pharmacologic agents, identifying one or more cellular responses to the one or more biologic or pharmacologic agents, and comparing the one or more cellular responses of the mammalian internal mammary artery-derived cell cultures from individuals in the statistically significant population. The mammalian internal mammary artery-derived cell of the invention can be used in vitro to screen a wide variety of compounds for effectiveness and cytotoxicity of pharmaceutical agents, growth/regulatory factors, and anti-inflammatory agents. To this end, the cells of the invention, or tissue cultures described above, are maintained in vitro and exposed to the compound to be tested. The activity of a cytotoxic compound can be measured by its ability to damage or kill cells in culture. This can readily be assessed by vital staining techniques. The effect of growth/regulatory factors can be assessed by analyzing the number of living cells in vitro, e.g., by total cell counts and differential cell counts. This can be accomplished using standard cytological and/or histological techniques, including the use of immunocytochemical techniques employing antibodies that define type-specific cellular antigens.

The cells and tissues of the invention can be used as model systems for the study of physiological or pathological conditions. The cells and tissues of the invention can also be used to study the mechanism of action of cytokines, growth factors, e.g., inflammatory mediators, e.g., IL-1, TNF and prostaglandins. In addition, cytotoxic and/or pharmaceutical agents can be screened for those that are most efficacious for a particular patient, such as those that reverse, reduce or prevent arthrosclerosis and other cardiovascular pathologies. Agents that prove to be efficacious in vitro could then be used to treat the patient therapeutically.

In another embodiment, iMACs can be administered in conjunction with an acceptable matrix, e.g., a pharmaceutically acceptable matrix. The matrix can be biodegradable. The matrix can also provide additional genetic material, cytokines, growth factors, or other factors to promote growth and differentiation of the cells. The cells can also be encapsulated prior to administration. The encapsulated cells can be contained within a polymer capsule. The polymers used to prepare carrier devices, scaffolds, or matrices described herein are biodegradable and biocompatible. The biodegradable polymers readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body. The expanded cell preparations of the invention comprising increased numbers of mammalian internal mammary artery-derived cells can be used to construct tissue-engineered devices such as a bioartificial blood vessel or other cardiovascular device. The cells can be combined with, or seeded onto scaffolds composed of natural of synthetic polymers.

These devices can then be implanted into a diseased or injured animal or human patient. The mammalian internal mammary artery derived cells can also be utilized within a device for the promotion of neovascularization, cell survival and tissue repair. An important challenge in the field of tissue engineering/organ reconstruction is how to adequately vascularize the therapeutic device. For any construct to be of value it must be generated in such a way that it contains a microvascular component. These capillaries would ensure that the construct has an adequate supply of nutrients, proper gas exchange and waste removal. iMACs have pro-angiogenic activity any may have value for tissue engineering applications.

Another application of gene therapy permits the use of a drug in a high concentration, which is normally considered to be dangerous, by providing drug resistance to normal mammalian internal mammary artery-derived cells by transferring a drug resistant gene into the cells. In particular, it is possible to carry out the treatment using an anticancer drug in high concentration by transferring a gene having drug resistance against the anticancer drug, e.g., transferring a multiple drug resistant gene into an expanded cell preparation comprising mammalian internal mammary artery-derived cells. A deficient protein can also be induced and expressed by transferring a gene encoding a target protein into the mammalian internal mammary artery-derived cell under the control of a suitable promoter. The expression of the protein can be controlled to obtain the same activity as that obtained by the natural expression in vivo. It is also possible to insert a gene encoding a ribozyme, an antisense nucleic acid or the like or another suitable gene into the mammalian internal mammary artery-derived cell to control expression of a specific gene product in the cells or to inhibit susceptibility to diseases. For example, the mammalian internal mammary artery-derived cell can be subjected to gene modification to express an antisense nucleic acid or a ribozyme, which can prevent growth of pathogens in the target organ including, but not limited to, HIV, HTLV-I, and HTLV-II.

The invention features a method for identifying agents, which influence the proliferation, differentiation, or survival of cells that have the potential to form mammalian internal mammary artery-derived cells. Examples of such agents are small molecules, antibodies, and extracellular proteins. Identified agents can be profiled and assessed for safety and efficacy in animals. In another aspect, the invention contemplates methods for influencing the proliferation, differentiation, or survival of cells that have the potential to form a mammalian internal mammary artery-derived cell by contacting the cells with an agent or agents identified by the foregoing method. The identified agents can be formulated as a pharmaceutical preparation.

It is preferred that the differentiated cells be derived from the patient that is being treated so as to avoid immune rejection. However, where autologous cells are not available, it can be useful to encapsulate the differentiated cells in a capsule that is permeable to nutrients and oxygen required by the cell and therapeutic factors the cell is secreting, yet impermeable to immune humoral factors and cells. Preferably the encapsulant is hypoallergenic, is easily and stably situated in a target tissue, and provides added protection to the implanted structure.

Protection from immune rejection can also be provided by genetic modification of the differentiated cells, according to any method known in the art. Autoantibody and CTL resistant cells can be produced using methods such as those disclosed in U.S. Pat. Nos. 5,286,632, 5,320,962, 5,342,761; and in WO1990/11354, WO1992/03917, WO1993/04169, and WO1995/17911. Alternatively, selection of resistant trans- differentiated cells is accomplished by culturing these cells in the presence of autoantibody or IDD associated CTLs or CTLs activated with IDD specific autoantigens. As a result of these techniques, cells having increased resistance to destruction by antibody or T-lymphocyte dependent mechanisms are generated. Such cells can be implanted into an appropriate host in an appropriate tissue as disclosed herein and have increased resistance to destruction by autoimmune processes.

Likewise, the human leukocyte antigen (HLA) profile of the differentiated cell can be modified, optionally by an iterative process, in which the differentiated cell is exposed to normal, allogeneic lymphocytes, and surviving cells selected. Alternatively, a site directed mutagenesis approach is used to eliminate the HLA markers from the surface of the differentiated cells, and modified differentiated cells thereby generated are implanted into a recipient mammal in need of such implantation.

A mammalian internal mammary artery-derived cell of the invention can be cryopreserved and maintained or stored in a "cell bank". Cryopreservation of cells of the invention can be carried out according to known methods. For example, but not by way of limitation, cells can be suspended in a "freeze medium" such as, culture medium further comprising 0 to 95 percent FBS and 0 to 10 percent dimethylsulfoxide (DMSO), a cryoprotectant, with or without 5 to 10 percent glycerol, at a density, for example, of about 0.5 to $10 \times 10^6$ cells per milliliter. Alternatively, other cryoprotectants may be used such as, carbohydrates including, but not limited to glucose, sucrose, maltose, and trehalose. The cells are dispensed into glass or plastic ampoules or other vessels that are then sealed and transferred to the freezing chamber of a controlled rate freezer. The optimal rate of freezing can be determined empirically. A programmable rate freezer for example, can give a change in temperature of −1 to −10° C. per minute through the heat of fusion can be used. Once the ampoules have reached −180° C., they are transferred to a liquid nitrogen storage area. Cryopreserved cells can be stored for a period of years, though they should be checked at least every 5 years for maintenance of viability. The cryopreserved cells of the invention constitute a bank of cells, portions of which can be "withdrawn" by thawing and then used as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10 percent FBS. Alternatively, a whole internal mammary artery or an internal mammary artery cut into segments or minced into pieces may be cryopreserved in a similar fashion. The mammalian internal mammary artery-derived cells may then be isolated from the thawed whole artery, artery segment(s) or minced artery pieces.

In a further embodiment, the mammalian internal mammary artery-derived cells of the invention can be cultured in vitro to produce conditioned media or cell lysate in high yield. For example, such cells, which either naturally produce a particular biological product of interest (e.g., a growth factor, regulatory factor, or peptide hormone), or have been genetically engineered to produce a biological product, could be clonally expanded using, for example, a three-dimensional cell culture system. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and HPLC, to name but a few. A "bioreactor" can be used to take advantage of the flow method for feeding, for example, a three-dimensional culture in vitro. Essentially, as fresh media is passed through the three-dimensional culture, the biological product is washed out of the culture and can then be isolated from the outflow, as above. Alternatively, a biological product of interest can remain within the cell and, thus, its collection can require that the cells be lysed. The biological product can then be purified using any one or more of the above-listed techniques.

EXAMPLE 1

Cell Isolation Optimization

Initial experiments were conducted to determine the optimal time necessary for tissue digestion. A five centimeter portion of the human internal mammary artery was obtained from the National Disease Research Interchange (NDRI, Philadelphia, Pa.). The artery was trimmed and washed in Dulbecco's modified Eagles medium (DMEM-low glucose; Invitrogen, Carlsbad, Calif.) or phosphate buffered saline (PBS; Invitrogen) to remove blood and debris. The entire artery was then transferred to a 50-milliliter conical tube.

The tissue was then digested, for varying amounts of time in an enzyme mixture containing 0.25 Units/milliliter collagenase (Serva Electrophoresis, Heidelberg, Germany) and 2.5 Units/milliliter dispase (Roche Diagnostics Corporation, Indianapolis Ind.). The enzyme mixture was then combined with endothelial growth medium −2 (EGM-2) (Lonza, Walkersville, Md.). The conical tube containing the tissue, EGM-2 and digestion enzymes was incubated at 37° C. in an orbital shaker at 225 rpm for increasing amounts of time (30, 60, 90, 120, 150 minutes). At the end of each time interval, cells were isolated from the resulting digested material. The partially digested artery was then transferred to a 50 mL conical tube containing a mixture of fresh enzymes and EGM-2 and further digested at 37° C. for the remaining time intervals. At the end of each time interval, the resulting digest was centrifuged at 150×g for 5 minutes, the supernatant was aspirated. The pellet was resuspended in 20 milliliters of EGM-2. The cell suspension was then filtered through a 70-micron nylon BD FALCON Cell strainer (BD Biosciences, San Jose, Calif.). The filtrate was then resuspended in EGM-2 (total volume 50 milliliters) and centrifuged at 150×g for 5 minutes. The supernatant was aspirated and the cells were resuspended in another 15 milliliters of fresh EGM-2 and plated into a tissue culture flask that was coated with 50 ug/cm$^2$ rat-tail type I collagen (Inamed, Freemont, Calif.). The cells were then cultured at 37° C. and 5% $CO_2$. Growth potential was then evaluated. Cells isolated were plated at 5000 cells/cm$^2$ onto type I rat tail collagen coated T75 flasks in EGM-2 and cultured at 37° C. in 5% carbon dioxide. Cells were passaged every 3-5 days. At each passage, cells were harvested with TypleLE (Invitrogen), counted and viability was measured using a Guava instrument (Guava Technologies, Hayward, Calif.). Population doublings [ln (final cell yield/initial number of cells plated)/ln 2] were then calculated.

Figure 6:
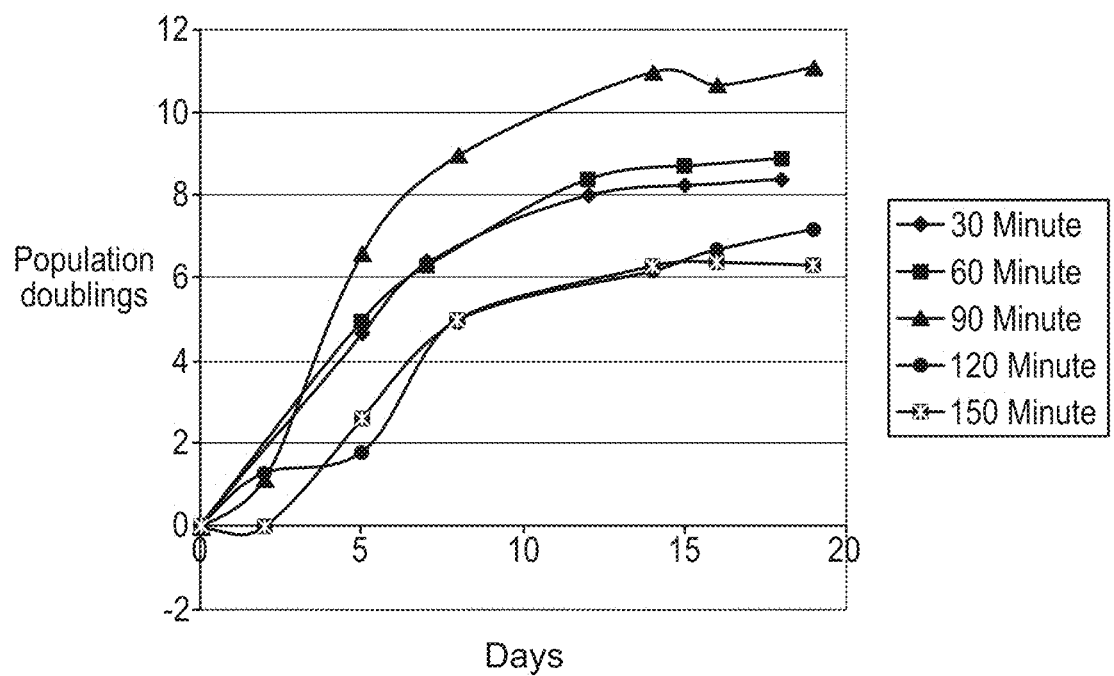
FIG. 6: Growth kinetics. Cells were isolated from an internal mammary artery that was exposed to digestion enzymes for 30, 60, 90, 120, 150 minutes. The cells derived from each of these time points were then cultured on tissue culture plates until cells reached senescence. Senescence was determined when the cells failed to achieve one population doubling during the growth interval. Cumulative population doublings (PD) was determined.

Data showed that the cells could be isolated from the internal mammary artery by sequentially digesting the artery. The cells obtained from the 30 or 60-minute time interval grew poorly (FIG. 6). Cells isolated from the 90-minute time interval were shown to have maximal growth potential. We determined therefore that the artery must initially be digested for about sixty minutes to remove external debris and the intimal layer of the artery. After the initial 60 minute digestion, the artery must then be transferred to a fresh enzyme mixture and further digested for an additional 30-60 minutes to obtain the cells that had maximum growth potential. This sequential digestion method allows for the isolation of a cell that is located within the adventitial/medial layer of the artery while excluding any cells from the intimal layer of the artery and from any external debris leftover from harvesting the artery.

EXAMPLE 2

Isolation of Human Internal Mammary Artery-Derived Cells

The optimal digestion time interval (described in Example 1) was then applied to isolate internal mammary artery-derived cells. A five centimeter portion of the human internal mammary artery was obtained from the National Disease Research Interchange (NDRI, Philadelphia, Pa.). The artery was trimmed and washed in Dulbecco's modified Eagles medium (DMEM-low glucose; Invitrogen, Carlsbad, Calif.) or phosphate buffered saline (PBS; Invitrogen) to remove blood and debris. The entire artery was then transferred to a 50-milliliter conical tube.

The tissue was then digested in an enzyme mixture containing 0.25 Units/milliliter collagenase (Serva Electrophoresis, Heidelberg, Germany) and 2.5 Units/milliliter dispase (Roche Diagnostics Corporation, Indianapolis Ind.). The enzyme mixture was then combined with iMAC Growth Medium (Advanced DMEM/F12 (Gibco), L-glutamine (Gibco) penicillin (50 Units/milliliter) and streptomycin (50 ug/mL, Gibco)) containing 10% fetal bovine serum (FBS)). The conical tube containing the tissue, iMAC Growth Medium and digestion enzymes was incubated at 37° C. in an orbital shaker at 225 rpm for 1 hour. The partially digested artery was then transferred to a 50 mL conical tube containing a mixture of fresh enzymes and iMAC Growth Medium and further digested at 37° C. for 1 hour. The digested artery was then removed from the 50 mL conical tube and discarded. The resulting digest was then centrifuged at 150×g for 5 minutes, the supernatant was aspirated. The pellet was resuspended in 20 milliliters of iMAC Growth Medium. The cell suspension was then filtered through a 70-micron nylon BD FALCON Cell strainer (BD Biosciences, San Jose, Calif.). The filtrate was then resuspended in iMAC Growth Medium (total volume 50 milliliters) and centrifuged at 150×g for 5 minutes. The supernatant was aspirated and the cells were resuspended in another 15 milliliters of fresh iMAC Growth Medium and plated into a tissue culture flask that was coated with 50 ug/cm$^2$ rat-tail type I collagen (Inamed, Freemont, Calif.). The cells were then cultured at 37° C. and 5% $CO_2$. Cells were cultured for 2-10 passages and then cryopreseved at 1-2e$^6$ cells/mL of cryoprotectant solution (DMEM/F12, 10% FBS) using standard cryopreservation methods.

EXAMPLE 3

Human Internal Mammary Artery-Derived Cell Morphology

Fresh iMACs, isolated as described in Example 2, were plated at 5000 cells/cm$^2$ onto type I rat tail collagen coated T75 flasks in iMAC Growth Medium and cultured at 37° C. in 5% carbon dioxide. Cells were passaged every 3-5 days. At each passage, cells were harvested with TypleLE (Gibco), counted and viability was measured using a Guava instrument (Guava Technologies, Hayward, Calif.). For morphological evaluation, iMACs were assessed by light microscopy and morphological characteristics of the cells were observed using a Nikon microscope and LCD digital camera.

iMACs were assessed by light microscopy and morphological characteristics of the cells were observed using a Nikon Microscope and LCD digital camera (FIG. 1). Consistently, cultures of iMACs showed a fibroblastic morphology. Morphology was stable at late passage (Passage 23).

EXAMPLE 4

Human Internal Mammary Artery-Derived Cell Growth Potential

Figure 2:
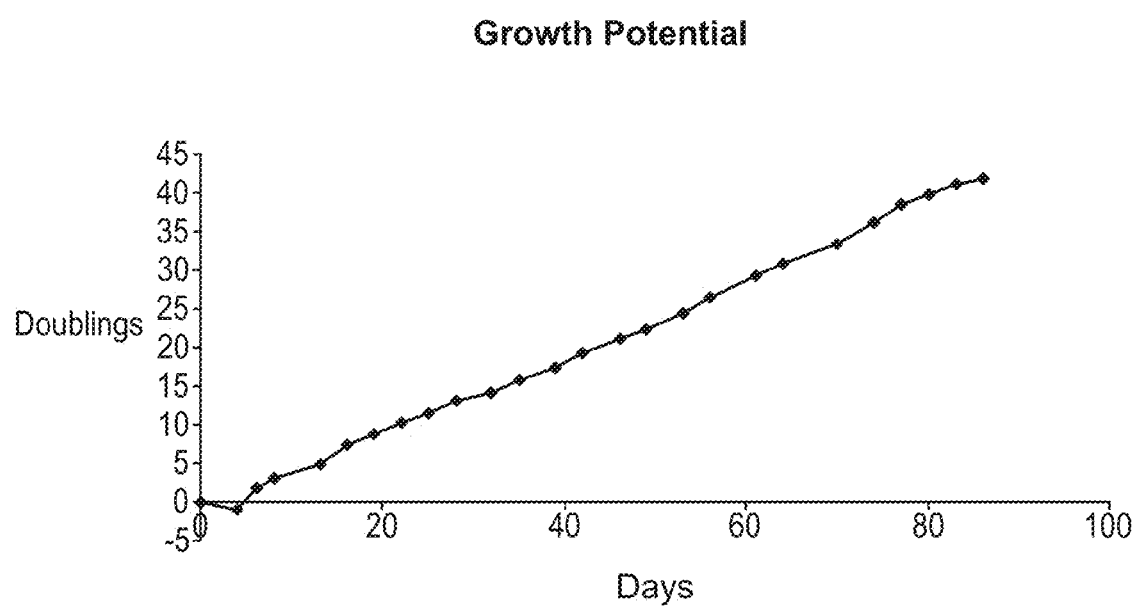
FIG. 2: Growth kinetics. iMACs were cultured on collagen-coated flasks for 81 days. Cells were harvested and counted every 3-5 days and population doubling was determined. Cultures were able to achieve at least 41.9 population doublings.
Figure 3:
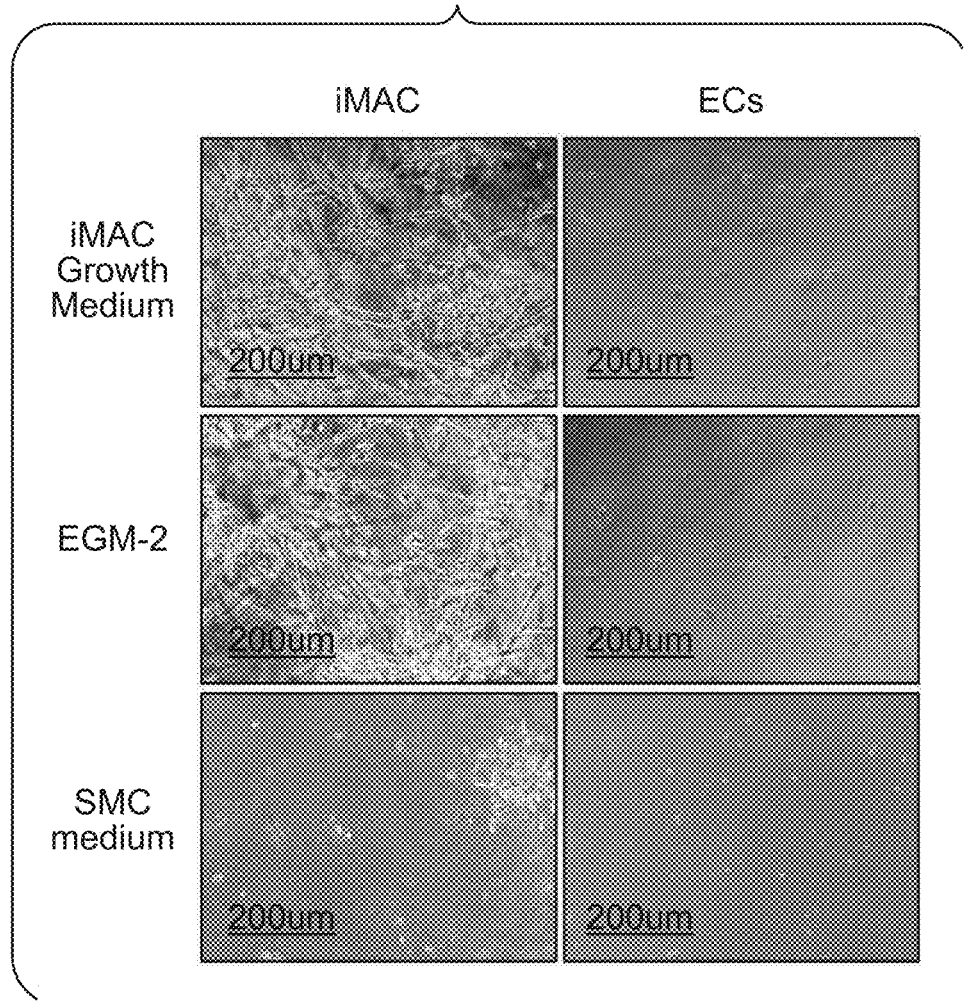
FIG. 3: Capillary formation. iMACs and human internal mammary artery endothelial cells (ECs) were cultured separately on Matrigel coated plates and capillary formation was observed. Cells were cultured in three different types of medium including, iMAC Growth Medium, endothelial growth medium-2 (EGM-2) or smooth muscle cell differentiation medium (SMC medium). Dense capillary formation was observed in cultures of iMACs grown in iMAC Growth Medium or EGM-2. Images were obtained at 100× magnification.

Fresh iMACs, isolated as described in Example 2, were plated at 5000 cells/cm$^2$ onto type I rat tail collagen coated T75 flasks in iMAC Growth Medium and cultured at 37° C. in 5% carbon dioxide. Cells were passaged every 3-5 days. At each passage, cells were harvested with TrypleLE (Gibco), counted and viability was measured using a Guava instrument (Guava Technologies, Hayward, Calif.). Population doublings [ln (final cell yield/initial number of cells plated)/ln 2] were then calculated. Cultures of iMACs were analyzed for ability to grow in culture (FIG. 2, Table 1). Cell populations were continually passaged for several months until senescence was reached. Senescence was determined when cells failed to achieve greater than one population doubling during the study time interval. After 86 days in culture, data shows that iMACs, grown in iMAC Growth Medium, on collagen-coated flasks can be propagated until at least passage 25 and achieve 41.9 population doublings. The average doubling time was 48 hours/doubling and greater than $10E^{18}$ cells can be obtained for one 5 cm long internal mammary artery.

TABLE 1

Growth kinetics. iMACs were cultured on collagen-coated flasks for 81 days. Cells were harvested and counted every 3-5 days and population doubling and viability was determined.

| | Passage | | | | | | |
|---|---|---|---|---|---|---|---|
| | 0 | 1 | 2 | 3 | 4 | 5 | 6 |
| Cells plated | nd | 4.13E+05 | 2.73E+05 | 1.00E+06 | 1.00E+06 | 1.00E+06 | 3.75E+05 |
| Cells harvested | 4.13E+05 | 2.73E+05 | 1.06E+06 | 2.15E+06 | 3.66E+06 | 5.89E+06 | 1.01E+06 |
| Viability | 96% | 97% | 98% | 99% | 98% | 99% | 99% |
| Days | 0 | 4 | 2 | 2 | 5 | 3 | 3 |
| Doublings | nd | −0.6 | 2.0 | 1.1 | 1.9 | 2.6 | 1.4 |
| Cumulative | 0 | 4 | 6 | 8 | 13 | 16 | 19 |
| Cumulative doublings | 0.0 | −0.6 | 2.0 | 3.1 | 5.0 | 7.6 | 9.0 |

| | Passage | | | | | | |
|---|---|---|---|---|---|---|---|
| | 7 | 8 | 9 | 10 | 11 | 12 | 13 |
| Cells plated | 3.75E+05 | 3.75E+05 | 3.75E+05 | 3.75E+05 | 3.75E+05 | 3.75E+05 | 3.75E+05 |
| Cells harvested | 1.07E+06 | 8.87E+05 | 1.10E+06 | 7.49E+05 | 1.21E+06 | 1.22E+06 | 1.30E+06 |
| Viability | 100% | 98% | 98% | 97% | 99% | 99% | 97% |
| Days | 3 | 3 | 3 | 4 | 3 | 4 | 3 |
| Doublings | 1.5 | 1.2 | 1.6 | 1.0 | 1.7 | 1.7 | 1.8 |
| Cumulative doublings | 22 | 25 | 28 | 32 | 35 | 39 | 42 |
| Cumulative doublings | 10.4 | 11.7 | 13.2 | 14.2 | 15.9 | 17.6 | 19.4 |

| | Passage | | | | | | |
|---|---|---|---|---|---|---|---|
| | 14 | 15 | 16 | 17 | 18 | 19 | 20 |
| Cells plated | 3.75E+05 | 3.75E+05 | 3.75E+05 | 3.75E+05 | 3.75E+05 | 3.75E+05 | 3.75E+05 |
| Cells harvested | 1.29E+06 | 8.78E+05 | 1.67E+06 | 1.52E+06 | 2.72E+06 | 1.12E+06 | 2.11E+06 |
| Viability | 98% | 98% | 100% | 100% | 98% | 98% | 95% |
| Days | 4 | 3 | 4 | 3 | 5 | 3 | 6 |
| Doublings | 1.8 | 1.2 | 2.2 | 2.0 | 2.9 | 1.6 | 2.5 |
| Cumulative doublings | 46 | 49 | 53 | 56 | 61 | 64 | 70 |
| Cumulative doublings | 21.2 | 22.4 | 24.6 | 26.6 | 29.5 | 31.0 | 33.5 |

| | Passage | | | | |
|---|---|---|---|---|---|
| | 21 | 22 | 23 | 24 | 25 |
| Cells plated | 1.00E+06 | 3.75E+05 | 3.75E+05 | 3.75E+05 | 3.75E+05 |
| Cells harvested | 6.76E+06 | 1.85E+06 | 9.80E+05 | 7.78E+05 | 6.61E+05 |
| Viability | 97% | 99% | 97% | 96% | 96% |
| Days | 4 | 3 | 4 | 3 | 3 |
| Doublings | 2.8 | 2.3 | 1.4 | 1.1 | 0.8 |
| Cumulative doublings | 74 | 77 | 80 | 83 | 86 |
| Cumulative doublings | 36.3 | 38.6 | 40.0 | 41.1 | 41.9 |

EXAMPLE 5

Human Internal Mammary Artery-Derived Cell In Vitro Capillary Formation

For capillary formation, passage 7, cryopreserved iMACs, isolated as described in Example 2, were thawed and seeded at 5000 cells/cm² onto Matrigel coated 24 well plates (BD Matrigel Matrix Cellware, BD Biosciences) and cultured in iMAC Growth Medium, endothelial growth medium-2 (Lonza) or smooth muscle differentiation medium (Lonza) for 3 days at 37° C. in 5% carbon dioxide. After 1-5 days in culture, capillary out growth was evaluated by light microscopy.

Figure 4:
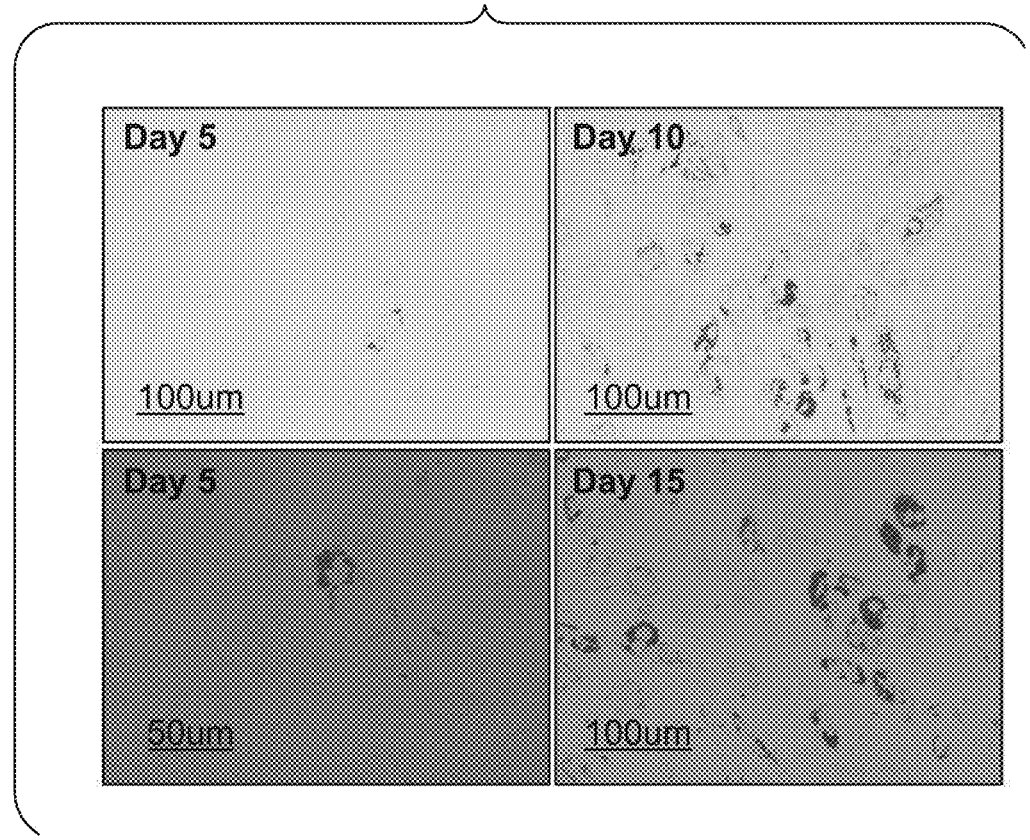
FIG. 4: Adipogenesis. iMACs were cultured in adipogenesis induction medium for 15 days. Cultures were fixed and stained with Oil Red-0 on days 5, 10, and 15-post induction. Lipid droplets within the cells stain red. Image of day 5 culture shown in lower left panel was obtained at 400× magnification. All other images were obtained at 200× magnification.

FIG. 4 shows that iMACs, cultured on Matrigel within iMAC Growth Medium or endothelial growth medium-2, differentiated into a dense network of capillary-like structures. iMACs did not differentiate within smooth muscle cell differentiation medium. Human thoracic artery derived endothelial cells (Cell Applications, Inc. San Diego, Calif.) were also cultured on Matrigel coated plates. These cells failed to differentiate into capillary structures, indicating that capillary differentiation is unique to iMACs.

EXAMPLE 6

Human Internal Mammary Artery-Derived Cell Adipogenesis

For adipogenesis differentiation, passage 7, cryopreseved iMACs, isolated as described in Example 2 were thawed and plated at 5000 cells/cm² onto non-coated or type I rat tail collagen coated 12 well plates and cultured in iMAC Growth Medium at 37° C. in 5% carbon dioxide. When the cells reached near-confluence, iMAC Growth Medium was replaced with adipogenic induction medium (Lonza) and further cultured for 15-20 days, with media exchange every 2-4 days. To determine the extent of adipogenic differentiation, cells were fixed with 10% formalin, stained with Oil-Red-0 (Sigma) and imaged on Day 5, 10 and 15 post induction.

Figure 5:
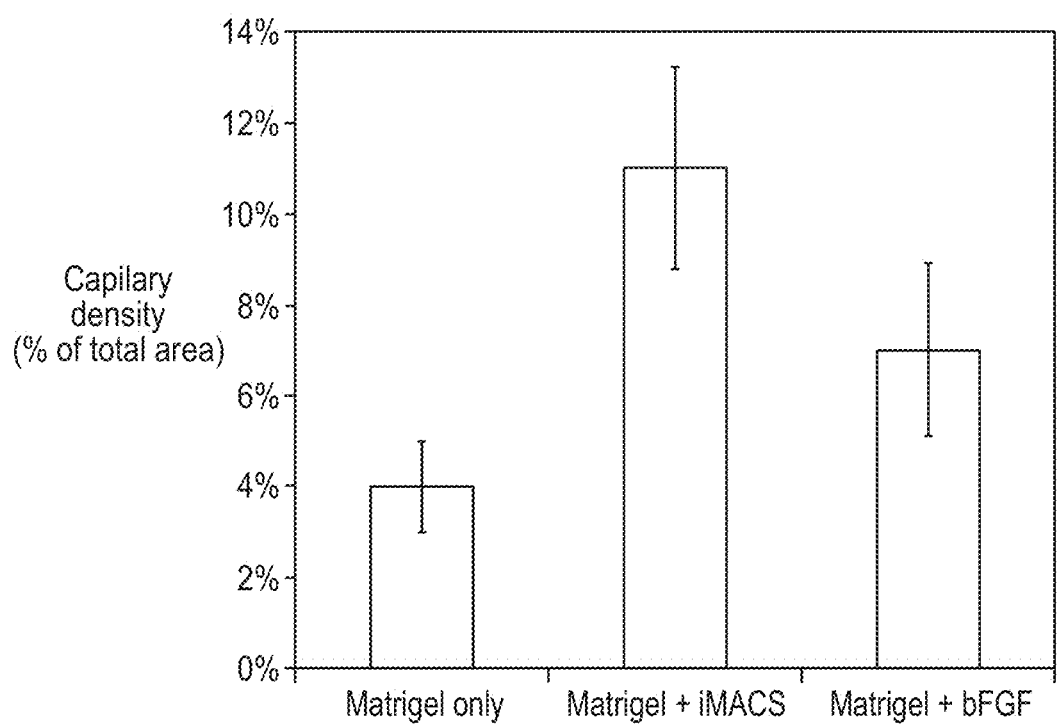
FIG. 5: Cellular infiltration/capillary density. Data bars represent the mean percentage of area comprised of cells/capillaries per total area evaluated. N=5 or 6. Error bars represent standard error of the mean (SEM).

Cultures of iMACs demonstrated significant adipocyte differentiation. FIG. 5 shows that iMACs, cultured within adipogenesis induction medium, produced many cells that stain positive with Oil Red-O. Few Oil Red-O positive cells are present after five days of induction. However, after ten days the number of Oil Red-O positive cells increased. After fifteen days, most of the cells within the culture differentiated into adipocytes.

EXAMPLE 7

Human Internal Mammary Artery-Derived Cell Surface Marker Phenotype

Flow cytometry analysis was performed on fresh iMACs isolated as described in Example 2. Cells were expanded to passage seven in growth medium on type I collagen coated T75 flasks at 37° C. and 5% carbon dioxide. Adherent cells were washed in PBS and detached with TypleLE (Gibco). Cells were harvested, centrifuged and resuspended in 3% (v/v) FBS in PBS at a concentration of $1\times10^7$ cells/mL. Each specific antibody was added to 100 microliters of cell suspension and the mixture was incubated in the dark for 30-60 minutes at 4° C. After incubation, cells were washed with PBS and centrifuged to remove excess antibody. Cells were resuspended in 300 microliters PBS and analyzed by flow cytometry. Flow cytometry analysis was performed with a Guava instrument. Antibodies used are shown in Table 2.

TABLE 2

Antibodies used in characterizing cell surface markers of iMACs.

| Antibody | Manufacture | Catalog number |
| --- | --- | --- |
| CD34 | BD Pharmingen | 555821 |
| CD44 | BD Pharmingen | 555478 |
| CD45R | BD Pharmingen | 555489 |
| CD117 | BD Pharmingen | 340529 |
| CD141 | BD Pharmingen | 559781 |
| CD31 | BD Pharmingen | 555446 |
| CD133 | Miltenyi Biotech | 120-001-243 |
| SSEA4 | R&D Systems | FAB1435P |
| CD105 | SantaCruz Biotech | SC-21787 |
| CD104 | BD Pharmingen | 555720 |
| CD166 | BD Pharmingen | 559263 |
| CD29 | BD Pharmingen | 555442 |
| IgG-FITC | BD Pharmingen | 555748 |
| IgG-PE | BD Pharmingen | 555749 |
| CD34 | BD Pharmingen | 555821 |
| CD44 | BD Pharmingen | 555478 |
| CD45R | BD Pharmingen | 555489 |
| CD117 | BD Pharmingen | 340529 |
| CD141 | BD Pharmingen | 559781 |
| CD31 | BD Pharmingen | 555446 |
| CD49c | BD Pharmingen | 556025 |
| CD73 | BD Pharmingen | 550257 |
| CD90 | BD Pharmingen | 555596 |
| HLA-I | BD Pharmingen | 555553 |
| HLA-II | BD Pharmingen | 555558 |
| CD133 | Miltenyi Biotech | 120-001-243 |
| SSEA4 | R&D Systems | FAB1435P |
| CD105 | SantaCruz Biotech | SC-21787 |
| CD104 | BD Pharmingen | 555720 |
| CD166 | BD Pharmingen | 559263 |
| CD29 | BD Pharmingen | 555442 |
| CD24 | BD Pharmingen | 555428 |
| CD56 | AbCAM | MEM188 |
| CD138 | BD Pharmingen | 550805 |
| E-cadherin | BD Pharmingen | 612130 |
| IgG-FITC | BD Pharmingen | 555748 |
| IgG-PE | BD Pharmingen | 555749 |

TABLE 3 iMACs were characterized by flow cytometry (Table 3). Passage seven cultures of iMACs showed positive staining for CD29, CD44, CD73, CD166 and HLA-1 and negative staining for CD10, CD15, CD23, CD24, CD31, CD34, CD45, CD62p, CD80, CD86, CD104, CD105, CD117, CD133, CD138, Cd141, VE-Cadherin, KDR/Flk-1 and HLA-2. Table 3 compares the observed iMAC surface marker phenotype to the surface marker phenotype of known cell types.

| Cell type | Antibody | Cell-type expression | iMAC expression |
| --- | --- | --- | --- |
| Enothelial progenitor cells | CD34 | Positive | Negative |
| | CD133 | Positive | Negative |
| | CD45 | Positive | Negative |
| Endothelial cells | VE Cadherin | Positive | Negative |
| | KDR/Flk1 | Positive | Negative |
| | CD31 | Positive | Negative |
| | CD104 | Positive | Negative |
| Smooth muscle cells | CD141 | Positive | Negative |
| Mesenchymal stem cells | CD10 | Positive | Negative |
| | CD29 | Positive | Positive |
| | CD44 | Positive | Positive |
| | CD73 | Positive | Positive |
| | CD105 | Positive | Negative |
| | CD166 | Positive | Positive |
| Other | CD15 | Positive | Negative |
| | CD23 | Positive | Negative |
| | CD24 | Positive | Negative |
| | CD62p | Positive | Negative |
| | CD73 | Positive | Positive |
| | CD80 | Positive | Negative |
| | CD86 | Positive | Negative |
| | CD117 | Positive | Negative |

TABLE 3-continued iMACs were characterized by flow cytometry (Table 3). Passage seven cultures of iMACs showed positive staining for CD29, CD44, CD73, CD166 and HLA-1 and negative staining for CD10, CD15, CD23, CD24, CD31, CD34, CD45, CD62p, CD80, CD86, CD104, CD105, CD117, CD133, CD138, Cd141, VE-Cadherin, KDR/Flk-1 and HLA-2. Table 3 compares the observed iMAC surface marker phenotype to the surface marker phenotype of known cell types.

| Cell type | Antibody | Cell-type expression | iMAC expression |
|---|---|---|---|
| | CD138 | Positive | Negative |
| | HLA 1 | Positive | Positive |
| | HLA 2 | Positive | Negative |

Table 3: Cell surface marker phenotype. iMACs were characterized by flow cytometry using the antibodies described in Table 1. Markers were organized according to known surface markers of specific cell types (Cell type). Surface markers expressed by the specific cell type (Cell-type expression). iMACs that express tested surface marker (Positive). Positive staining was determined by comparing test antibody staining profile to negative control antibody staining. Staining of greater than 75% of cells was considered positive. iMACs that do not express tested surface marker (Negative). Staining was considered negative if less than 25% cells were positive compared to a negative control antibody.

EXAMPLE 8

Human Internal Mammary Artery-Derived Cell Gene Expression

Cells isolated as described in Example 2, were plated at 5000 cells/cm² onto type I collagen coated T75 flasks in iMAC Growth Medium and cultured at 37° C. in 5% carbon dioxide. Cells were passaged every 3-5 days. At passage 10, near-confluent cultures were lysed directly on the flask using an RNA extraction kit (Qiagen, Valencia, Calif.) following the manufactures instructions. Total RNA was then extracted and gene expression was evaluated using Human Angiogenesis Oligo Arrays (SA Biosciences, Frederick, Md.) and Affymetrix Human Exon ST1.0 microarrays following the manufactures instructions An oligomeric hybridization array was used to characterize the genes expression profile of iMACs. Data shows that iMACs express 19 out of 118 tested angiogenesis related genes including; CD13, chemokine ligand 2, Ephrin A2, Ephrin A3, Endoglin, Endothelial PAS domain protein 1, Fibroblast growth factor-2, Fibroblast growth factor receptor-3, Hypoxia-inducible factor-1, Matrix metalenoprotinase-2, Neuropilin-1, Placental growth factor, Urokinase, Thrombospondin-2, TIMP inhibitor-1, TIMP inhibitor-3, TNF-12a, Troponin T type-1, VEGF-B and VEGF-C.

In addition, cultures of iMACs were evaluated by microarray analysis using Affymetrix Human Exon 1.0 microarrays. Table 4 shows the top 500 most expressed transcripts. Several developmentally regulated genes are highly expressed including, tripartite motif-containing 33 (TRIM33), SRY (sex determining region Y)-box 11 (SOX-11), Notch homolog 2 (*Drosophila*) (NOTCH-2), cysteine rich transmembrane BMP regulator 1 (CRIM-1), homeobox D9 (HOXD9) and POU class 3 homeobox 3 (POU3F3) (Table 5).

TABLE 4

Angiogenesis Related Gene Expression. Cultures of iMACs were evaluated by Oligomeric hybridization arrays and then evaluated using the software provided by the manufacturer. Global background value was obtained and then subtracted from the values obtained from the identified hybridization signals. Genes shown here are expressed by iMACs at a level above background values.

| UniGene | Description |
|---|---|
| Hs.311640 | Ribosomal protein S27a |
| Hs.525622 | V-akt murine thymoma viral oncogene homolog 1 |
| Hs.1239 | Alanyl (membrane) aminopeptidase, CD13 |
| Hs.303649 | Chemokine (C-C motif) ligand 2 |
| Hs.532655 | Ephrin-A2 |
| Hs.516656 | Ephrin-A3 |
| Hs.76753 | Endoglin (Osler-Rendu-Weber syndrome 1) |
| Hs.468410 | Endothelial PAS domain protein 1 |
| Hs.284244 | Fibroblast growth factor 2 (basic) |
| Hs.1420 | Fibroblast growth factor receptor 3 |
| Hs.509554 | Hypoxia-inducible factor 1 |
| Hs.512234 | Interleukin 6 (interferon, beta 2) |
| Hs.479756 | Kinase insert domain receptor |
| Hs.513617 | Matrix metallopeptidase 2 |
| Hs.131704 | Neuropilin 1 |
| Hs.252820 | Placental growth factor |
| Hs.77274 | Plasminogen activator, Urokinase |
| Hs.371147 | Thrombospondin 2 |
| Hs.522632 | TIMP metallopeptidase inhibitor 1 |
| Hs.652397 | TIMP metallopeptidase inhibitor 3 |
| Hs.355899 | Tumor necrosis factor receptor superfamily, member 12A |
| Hs.631558 | Troponin T type 1 (skeletal, slow) |
| Hs.78781 | Vascular endothelial growth factor B |
| Hs.435215 | Vascular endothelial growth factor C |

TABLE 5

Microarray Gene Expression Analysis. Passage 10 cultures of iMACs were evaluated using Affymetrix microarray Exon ST1.0 microarrays. 500 most highly expressed genes are shown iMACs were measured in triplicate (Sample 1, Sample 2, and Sample 3) are relative gene expression is represented by fluorescent intensity units. Global non-specific background fluorescence was subtracted each specific hybridization signal. The average fluorescence intensity of triplicate measurements (Average). Standard deviation (Std Dev).

| Probe Set ID | SAMPLE 1 | SAMPLE 2 | SAMPLE 3 | Gene Symbol | mRNA-Accession | AVERAGE | STD DEV |
|---|---|---|---|---|---|---|---|
| 2429144 | 14.42 | 14.47 | 14.51 | TRIM33 | NM_015906 | 14.5 | 0.05 |
| 2467968 | 13.90 | 13.90 | 14.10 | SOX11 | NM_003108 | 14.0 | 0.11 |
| 2431202 | 13.57 | 13.63 | 13.66 | NOTCH2 | NM_024408 | 13.6 | 0.05 |
| 2477142 | 13.19 | 13.25 | 13.18 | CRIM1 | NM_016441 | 13.2 | 0.04 |
| 2516866 | 12.80 | 12.91 | 12.91 | HOXD9 | NM_014213 | 12.9 | 0.07 |
| 2497821 | 12.41 | 12.59 | 12.37 | POU3F3 | NM_006236 | 12.5 | 0.12 |

EXAMPLE 9

Human Internal Mammary Artery-Derived Cell Trophic Factor Analysis

Fresh iMACs, isolated as described in Example 2, were cultured to passage 7 and then seeded onto a type I collagen coated six well plates at 5000 cells/cm² in iMAC Growth Medium and cultured at 37° C. and 5% carbon dioxide. Spent culture medium was then changed to a serum-free medium (DMEM-low glucose (Gibco), penicillin (50 Units/milliliter) and streptomycin (50 ug/mL)) and further cultured for 20 hours. Conditioned, serum-free medium was collected by centrifugation at 14,000×g for 5 minutes and stored at −20° C.

Samples were then analyzed using the HumanMAP v1.6 Immunoplex Immunoassay (Rules-Based Medicine, Austin, Tex.). Trophic factor analysis was performed on three independent cultures of iMACs and normalized to values obtained for unconditioned serum-free culture medium.

The secretion of ninety different growth factors and cytokines were analyzed on cultures of iMACs (Table 6, Table 7). Results show that iMACs secrete elevated levels of β2 microglobulin, cancer antigen 19-9, creatine kinase-MB, ENA-78, endothelin-1, eotaxin, fatty acid binding protein, ferritin, basic FGF, interleukin-6, interleukin-8, insulin, MCP-1, PAI-1, stem cell factor, TIMP-1, VCAM-1 and VEGF. iMACs do not secrete Von Willebrand factor.

TABLE 6

Trophic factor secretion profile. Serum free culture medium derived from cultures of iMACs was evaluated for growth factor and cytokine secretion. Amount of factor shown from three independent cultures (iMAC 1, iMAC 2, iMAC 3) was normalized to cell number and expressed as amount of factor secreted per million cells per 20 hours. Assay detection limit (Least Detectable Dose). Unconditioned culture medium (No cell control).

| | Analytes | | | | |
|---|---|---|---|---|---|
| | Alpha-1 Antitrypsin | Adiponectin | Alpha-2 Macroglobulin | Alpha-Fetoprotein | Apolipoprotein A1 |
| Units | mg/mL | ug/mL | mg/mL | ng/mL | mg/mL |
| Least Detectable Dose | 5.3E−08 | 0.0010 | 0.00030 | 0.086 | 3.3E−08 |
| iMAC 1 | 8.4E−07 | 9.4E−03 | 5.7E−04 | 2.2E+00 | 4.7E−07 |
| iMAC 2 | 2.5E−06 | 2.4E−02 | 1.9E−03 | 5.1E+00 | 1.4E−06 |
| iMAC 3 | 3.3E−07 | 5.0E−03 | 4.8E−04 | 9.4E−01 | 2.8E−07 |
| No cell control | 4.6E−08 | 0.00051 | 4.3E−05 | 0.18 | 3.7E−08 |

| | Analytes | | | | |
|---|---|---|---|---|---|
| | Apolipoprotein CIII | Apolipoprotein H | Beta-2 Microglobulin | Brain-Derived Neurotrophic Factor | Complement 3 |
| Units | ug/mL | ug/mL | ug/mL | ng/mL | mg/mL |
| Least Detectable Dose | 1.4E−05 | 4.4E−05 | 6.6E−05 | 0.0059 | 2.6E−08 |
| iMAC 1 | 4.2E−04 | 1.2E−03 | 2.7E−01 | 2.3E−02 | 9.3E−05 |
| iMAC 2 | 9.9E−04 | 3.1E−03 | 6.4E−01 | 1.0E−01 | 2.5E−04 |
| iMAC 3 | 2.6E−04 | 5.8E−04 | 1.4E−01 | 1.4E−02 | 4.5E−05 |
| No cell control | 1.6E−05 | 0.00016 | 0.00043 | nd | 1.1E−07 |

| | Analytes | | | | |
|---|---|---|---|---|---|
| | Cancer Antigen 125 | Cancer Antigen 19-9 | Calcitonin | CD40 | CD40 Ligand |
| Units | U/mL | U/mL | pg/mL | ng/mL | ng/mL |
| Least Detectable Dose | 0.84 | 0.049 | 1.2 | 0.0042 | 0.0040 |
| iMAC 1 | 1.6E+01 | 6.3E+00 | 6.8E+00 | nd | Nd |
| iMAC 2 | 6.0E+01 | 1.7E+01 | 1.7E+01 | nd | Nd |
| iMAC 3 | nd | 3.7E+00 | 3.2E+00 | nd | 5.2E−03 |
| No cell control | nd | nd | nd | nd | Nd |

| | Analytes | | | | |
|---|---|---|---|---|---|
| | Carcinoembryonic Antigen | Creatine Kinase-MB | C Reactive Protein | EGF | ENA-78 |
| Units | ng/mL | ng/mL | ug/mL | pg/mL | ng/mL |
| Least Detectable Dose | 0.17 | 0.084 | 7.7E−06 | 1.5 | 0.015 |
| iMAC 1 | 2.1E−01 | 1.1E+00 | nd | 1.3E+01 | 3.0E−01 |
| iMAC 2 | 5.3E−01 | 3.5E+00 | 5.8E−05 | 5.2E+01 | 7.3E−01 |
| iMAC 3 | 9.7E−02 | 4.8E−01 | nd | 1.0E+01 | 1.2E−01 |
| No cell control | nd | 0.0079 | nd | nd | 0.0034 |

TABLE 6-continued

Trophic factor secretion profile. Serum free culture medium derived from cultures of iMACs was evaluated for growth factor and cytokine secretion. Amount of factor shown from three independent cultures (iMAC 1, iMAC 2, iMAC 3) was normalized to cell number and expressed as amount of factor secreted per million cells per 20 hours. Assay detection limit (Least Detectable Dose). Unconditioned culture medium (No cell control).

| | Analytes | | | | |
|---|---|---|---|---|---|
| | Endothelin-1 | EN-RAGE | Eotaxin | Erythropoietin | Fatty Acid Binding Protein |
| Units | pg/mL | ng/mL | pg/mL | pg/mL | ng/mL |
| Least Detectable Dose | 1.4 | 0.0050 | 8.2 | 33 | 0.60 |
| iMAC 1 | 5.9E+01 | nd | 3.9E+03 | nd | 1.3E+01 |
| iMAC 2 | 1.6E+02 | nd | 1.2E+04 | nd | 3.0E+01 |
| iMAC 3 | 3.6E+01 | nd | 2.6E+03 | nd | 5.5E+00 |
| No cell control | 2.6 | nd | 3.7 | nd | Nd |

| | Analytes | | | | |
|---|---|---|---|---|---|
| | Factor VII | Ferritin | FGF basic | Fibrinogen | G-CSF |
| Units | ng/mL | ng/mL | pg/mL | mg/mL | pg/mL |
| Least Detectable Dose | 0.20 | 0.0070 | 20 | 4.9E−08 | 1.0 |
| iMAC 1 | nd | 5.6E+00 | 1.1E+03 | nd | nd |
| iMAC 2 | nd | 1.4E+01 | 3.3E+03 | 6.1E−07 | nd |
| iMAC 3 | nd | 3.0E+00 | 7.2E+02 | nd | nd |
| No cell control | nd | 0.014 | 11 | nd | nd |

TABLE 6

Trophic factor secretion profile (Cont.). Serum free culture medium derived from cultures of iMACs was evaluated for growth factor and cytokine secretion. Amount of factor shown from three independent cultures (iMAC 1, iMAC 2, iMAC 3) was normalized to cell number and expressed as amount of factor secreted per million cells per 20 hours. Assay detection limit (Least Detectable Dose). Unconditioned culture medium (No cell control).

| | Analytes | | | | | | | | | |
|---|---|---|---|---|---|---|---|---|---|---|
| | Growth Hormone | GM-CSF | Glutathione S-Transferase | Haptoglobin | ICAM-1 | IFN-gamma | IgA | IgE | IGF-1 | IgM |
| Units | ng/mL | pg/mL | ng/mL | mg/mL | ng/mL | pg/mL | mg/mL | ng/mL | ng/mL | mg/mL |
| Least Detectable Dose | 0.027 | 11 | 0.081 | 1.3E−06 | 0.63 | 0.92 | 4.2E−08 | 2.8 | 0.80 | 7.6E−08 |
| iMAC 1 | nd | 4.9E+01 | 7.5E−01 | 2.9E−06 | 3.7E+00 | nd | 2.1E−05 | 1.2E+00 | nd | nd |
| iMAC 2 | nd | 1.3E+02 | 1.2E+00 | 7.0E−06 | 8.1E+00 | nd | 4.9E−05 | nd | nd | nd |
| iMAC 3 | 6.5E−02 | 1.5E+01 | 2.2E−01 | 1.4E−06 | 1.5E+00 | nd | 8.3E−06 | 5.6E−01 | nd | 3.4E−07 |
| No cell control | nd | 2.6 | nd | 3.5E−07 | 0.14 | nd | 3.0E−06 | nd | 6.1 | nd |

| | Analytes | | | | | | | | |
|---|---|---|---|---|---|---|---|---|---|
| | IL-10 | IL-12p40 | IL-12p70 | IL-13 | IL-15 | IL-16 | IL-18 | IL-1alpha | IL-1beta | IL-1ra |
| Units | pg/mL | ng/mL | pg/mL | pg/mL | ng/mL | pg/mL | pg/mL | ng/mL | pg/mL | pg/mL |
| Least Detectable Dose | 3.1 | 0.24 | 19 | 11 | 0.26 | 13 | 11 | 0.00050 | 0.29 | 3.0 |
| iMAC 1 | 3.1E+01 | 6.8E−01 | 1.6E+02 | 8.2E+01 | 1.8E+00 | nd | 3.0E+01 | 1.1E−02 | 8.9E−01 | nd |
| iMAC 2 | 6.4E+01 | 8.5E−01 | 4.5E+02 | 2.0E+02 | 4.2E+00 | nd | 5.5E+01 | 2.8E−02 | 3.7E+00 | nd |
| iMAC 3 | 1.4E+01 | 2.7E−01 | 6.5E+01 | 3.8E+01 | 8.2E−01 | nd | 1.0E+01 | nd | 4.1E−01 | nd |
| No cell control | 3.0 | 0.046 | 17 | 8.0 | 0.15 | nd | nd | 0.00079 | nd | 7.6 |

| | Analytes | | | | | | | | |
|---|---|---|---|---|---|---|---|---|---|
| | IL-2 | IL-3 | IL-4 | IL-5 | IL-6 | IL-7 | IL-8 | Insulin | Leptin | Lipoprotein (a) |
| Units | pg/mL | ng/mL | pg/mL | pg/mL | pg/mL | pg/mL | pg/mL | uIU/mL | ng/mL | ug/mL |
| Least Detectable Dose | 12 | 0.035 | 21 | 6.5 | 2.4 | 11 | 0.70 | 0.17 | 0.021 | 0.019 |
| iMAC 1 | 1.8E+01 | 6.0E−02 | 1.3E+02 | nd | 1.7E+04 | 1.8E+02 | 4.0E+02 | 2.4E+04 | 1.6E−01 | 8.6E−04 |
| iMAC 2 | nd | nd | 3.0E+02 | nd | 6.3E+04 | 4.7E+02 | 1.4E+03 | 5.1E+04 | 2.1E−01 | 2.2E−03 |
| iMAC 3 | nd | nd | 3.8E+01 | nd | 8.1E+03 | 9.9E+01 | 1.7E+02 | 8.0E+03 | 6.6E−02 | 5.0E−04 |
| No cell control | nd | nd | 15 | nd | Nd | 18 | 0.37 | 0.32 | nd | nd |

TABLE 7

Secreted factors. Serum free culture medium derived from cultures of iMACs was evaluated for growth factor and cytokine secretion. Secreted proteins shown. These are factors secreted in an amount that exceeds the no cell control unconditioned culture medium and assay detection limit value.

| Secreted proteins |
|---|
| β2 Microglobulin |
| Cancer Antigen 19-9 |
| Creatine Kinase-MB |
| ENA-78 |
| Endothelin-1 |
| Eotaxin |
| Fatty Acid Binding Protein |
| Ferritin |
| FGF basic |
| IL-6 |
| IL-8 |
| Insulin |
| MCP-1 |
| PAI-1 |
| Stem Cell Factor |
| TIMP-1 |
| VCAM-1 |
| VEGF |

EXAMPLE 10

Human Internal Mammary Artery-Derived Cell In Vivo Angiogenesis Activity

An important challenge in the field of tissue engineering/organ reconstruction is how to adequately vascularization the therapeutic device. For any construct to be of value it must be generated in such a way that it contains a microvascular component. These capillaries would ensure that the construct has an adequate supply of nutrients, proper gas exchange and waste removal. The identification of a cell that enhances neovascularization would be of great value.

We have recently isolated a cell from the human internal mammary artery termed internal mammary artery derived cells. These cells may have important pro-angiogenic properties. In this study, the Matrigel angiogenesis assay was used to evaluate pro-angiogenic activity of iMACs. The Matrigel angiogenesis assay has become the method of choice for many studies involving in vivo testing for angiogenesis. In this assay, angiogenesis-inducing compounds, such as bFGF, are introduced into cold liquid Matrigel. Then, after subcutaneous injection, the Matrigel solution solidifies and permits subsequent penetration by host cells that induce vascularization. Assessment of angiogenic reactions in the Matrigel plug is achieved by examination of histological preparations, stained to enhance the visibility of blood vessels and to permit the determination of vascular density in selected sections.

TABLE 8

Experimental design.

| Group Number | Number of Animals | Number of implants | Test Material |
|---|---|---|---|
| 1 | 3 | 6 | Matrigel only |
| 2 | 3 | 6 | Matrigel + iMACs |
| 3 | 3 | 6 | Matrigel + bFGF |

On the day of transplantation, passage 7 iMACs (prepared as described in Example 2) were thawed at 37° C., cultured until subconfluent, harvested and resuspended in phosphate buffered saline (without Ca2+, Mg2+). About 400 mL of ice-cold growth factor-reduced Matrigel matrix (Gibco cat#12760-021) will be premixed with 100 ul of PBS containing $1 \times 10^6$ iMACs. In addition, Matrigel containing 50-ng/mL basic fibroblast growth factor (bFGF) was tested as a positive control, and was prepared in a similar manner as the cell-loaded Matrigel test articles. Cells or bFGF, diluted in Matrigel, was kept on wet ice until the time of transplantation. All handling of the SCID mice must take place under a hood. The mice were individually weighed and induced by a chamber induction technique using inhalation anesthesia (Isoflurane at 5.0%), during surgery the animal was maintained with Isoflurane at a level between 1.5 and 2.5%. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position. 500 ul of cell suspension in Matrigel was injected subcutaneously into the right and left dorsal surface of the mouse using 23 G needle.

Capillary density within the Matrigel scaffold was assessed histologically at day 10 post-implantation. Gross examination was performed on any animals that died during the course of the study or were euthanized in moribund condition. Mice were euthanized at their designated intervals by CO2 inhalation. Gross observations of the implanted sites was recorded. The subcutaneous implantation sites with their overlying skin was excised. The subcutaneous implantation sites with their overlying skin was bisected. Half of the tissue was preserved in 10% buffered formalin fixative for paraffin embedding. Fixed specimens were sent to Paragon Bioservices (Baltimore Md.) for histological processing. Histological sections were generated and stained with H&E. In addition, sections were stained with human specific anti-vimentin (Dako) and anti-Von Willebrand factor antibodies. Capillary density/cellular in-growth was quantified, in a blinded fashion, by a Paragon technician. Briefly, five images were obtained for each Matrigel implant. Then the percentage of area occupied by newly formed cells/capillaries vs. total area of a predefined frame in Matrigel was determined (Table 9).

The degree of cellularity was determined for all Matrigel explants. As shown in FIG. 5 and Table 9, very few cells or capillaries (4% of the total Matrigel area) were observed within group 1 Matrigel only implant. However, compared to group 1, iMAC seeded Matrigel stimulated cellular infiltration and capillary formation. Cells and capillaries occupied 11%+/−2% of the iMAC seeded Matrigel implants. Cells and capillaries occupied 7%+/−1.9% of the bFGF positive control Matrigel implants.

The data indicates that iMACs promote cellular infiltration and stimulate angiogenesis and the formation of a microvasculature within a Matrigel scaffold. These cells may therefore have value in tissue engineering/organ reconstruction applications by providing a means to enhance neovascularization and the overall viability of an implantable biological device.

TABLE 9

Cell infiltration/capillary density: Five microscopic fields were imaged per explant was obtained and the area occupied by cells and capillaries was estimated and reported as fraction of the total area. (Area composed of cells/capillaries/total-evaluated area). The evaluator was blinded to group assignment. Refer to Table 1 for treatment group descriptions. Matrigel explant was not detected (NA). Data shown is summarized in graphical form in FIG. 5.

|   |   | Field 1 | Field 2 | Field 3 | Field 4 | Field 5 | Average | Overall AVG | SEM |
|---|---|---|---|---|---|---|---|---|---|
| Group 1 | Animal1 Left | 0.06 | 0.06 | 0.03 | NA | NA | 0.05 | | |
| | Animal1 Right | NA | NA | NA | NA | NA | NA | | |
| | Animal2 Left | 0.1 | 0.02 | 0.05 | 0.03 | 0.08 | 0.06 | | |
| | Animal2 Right | 0.01 | 0.01 | 0.01 | 0.02 | 0.06 | 0.02 | | |
| | Animal3 Left | 0.04 | 0.09 | 0.05 | 0.04 | 0.02 | 0.05 | | |
| | Animal3 Right | 0 | 0 | 0 | 0 | 0 | 0.00 | 0.04 | 0.0106 |
| Group 2 | Animal4 Left | 0.15 | 0.16 | 0.16 | 0.18 | 0.13 | 0.16 | | |
| | Animal4 Right | 0.12 | 0.11 | 0.11 | NA | NA | 0.11 | | |
| | Animal5 Left | 0.06 | 0.09 | 0.07 | 0.08 | 0.13 | 0.09 | | |
| | Animal5 Right | 0.1 | 0.06 | 0.06 | 0.05 | 0.09 | 0.07 | | |
| | Animal6 Left | 0.18 | 0.21 | 0.18 | 0.24 | 0.19 | 0.20 | | |
| | Animal6 Right | 0.06 | 0.04 | 0.04 | 0.07 | 0.06 | 0.05 | 0.11 | 0.0226 |
| Group 3 | Animal10 Left | 0.04 | 0.17 | 0.02 | 0.07 | 0.02 | 0.06 | | |
| | Animal10 Right | 0.04 | 0.08 | 0.08 | 0.1 | 0.1 | 0.08 | | |
| | Animal11 Left | 0.07 | 0.1 | 0.2 | 0.18 | NA | 0.14 | | |
| | Animal11 Right | 0.03 | 0.04 | 0.07 | 0.07 | 0.05 | 0.05 | | |
| | Animal12 Left | NA | NA | NA | NA | NA | NA | | |
| | Animal12 Right | 0.02 | 0.02 | 0.02 | NA | NA | 0.02 | 0.07 | 0.0194 |

EXAMPLE 11

Figure 7:
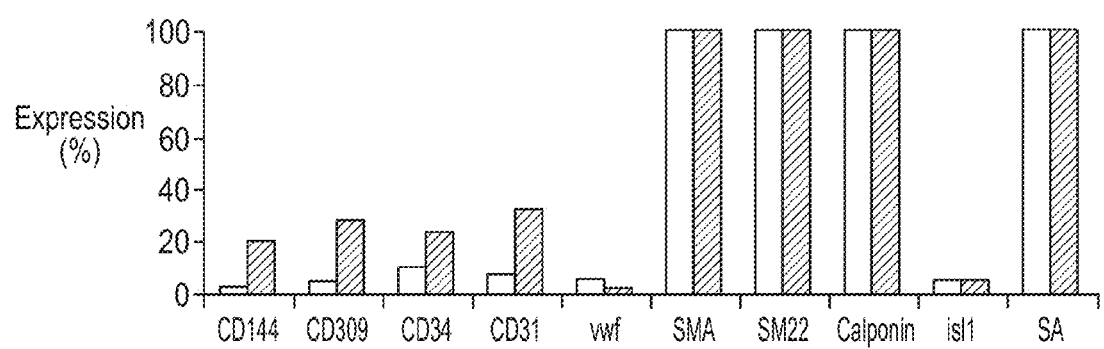
FIG. 7: Endothelial cell differentiation: iMACs up-regulate endothelial cell markers after treatment with endothelial differentiation medium. Expression (%) refers to the percentage of cells within the iMAC cell culture population that express the tested marker. Percentage of cells expressing the tested marker after growth in standard iMAC cell culture medium (white bars). Percentage of cells expressing the tested marker after growth in differentiation medium (black bars).

Human Internal Mammary Artery-Derived Cell Endothelial and Smooth Muscle Cell Differentiation iMACs have been shown to differentiate into capillary-like cells when cultured on Matrigel (see Example 5). Further studies were conducted to characterize iMAC endothelial cell, smooth muscle cell and cardiomyocyte differentiation. Cyropreserved, passage 17 iMACs were thawed and seeded onto tissue culture plastic and cultured in endothelial differentiation medium (DMEM+10% FBS+50 ng/ml VEGF) for seven days. Cells were then evaluated by flow cytometry for the expression of several different endothelial cell specific markers including; CD144, CD309, CD34, CD31 and Von Willebrand factor. Results showed that approximately 20% of the cultured iMACs upregulated the expression of CD144, CD309, CD31 and CD34 when cultured in endothelial cell differentiation medium (FIG. 7).

Figure 8:
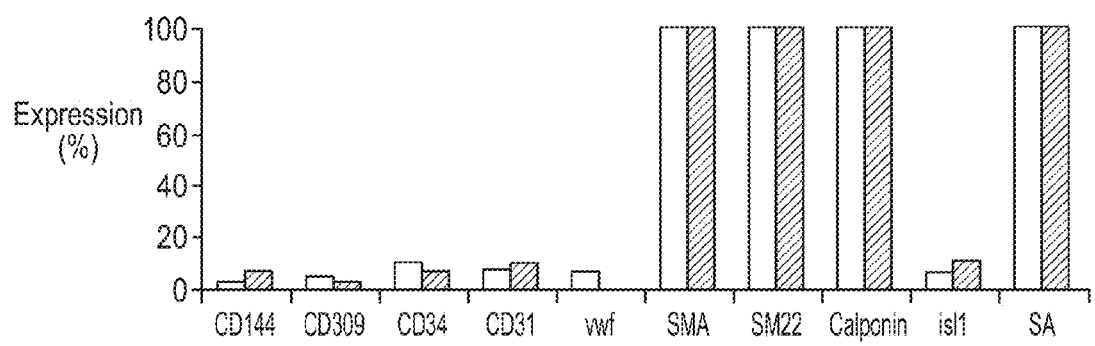
FIG. 8: Smooth muscle cell differentiation: Smooth muscle cell markers remain expressed before and after treatment with smooth muscle cell differentiation medium. Expression (%) refers to the percentage of cells within the iMAC culture population that express the tested marker. Percentage of cells expressing the tested marker after growth in standard iMAC cell culture medium (white bars). Percentage of cells expressing the tested marker after growth in differentiation medium (black bars).

Passage 17 iMACs were also thawed, seeded onto tissue culture plastic, cultured in smooth muscle differentiation medium (MesenPRO RS, Invitrogen for seven days and then evaluated by flow cytometry for three different smooth muscle cell specific markers including; SMA, SM22, Calponin. Results showed that iMACs expressed all three of these smooth muscle cell markers under standard iMAC growth conditions. The expression pattern is unaltered when cultured in smooth muscle cell differentiation medium (FIG. 8)

Figure 9:
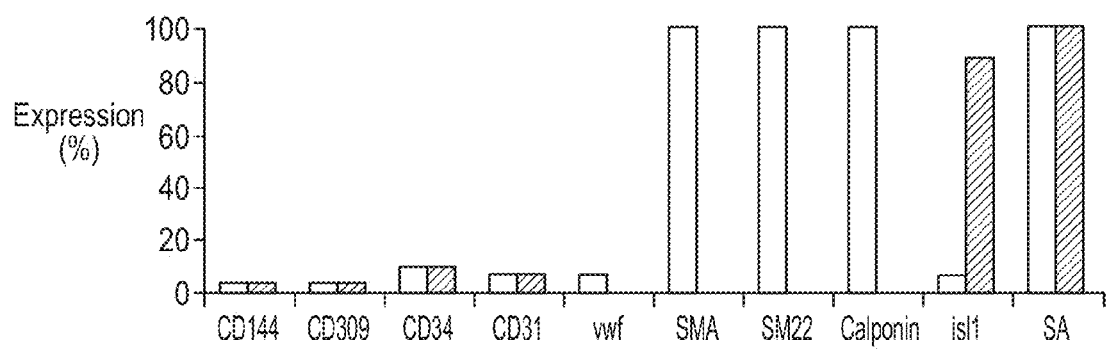
FIG. 9: Cardiomyocyte differentiation: The cardiomyocyte markers was upregulated after culturing iMACs in cardiomyocyte differentiation medium. Expression (%) refers to the percentage of cells within the iMAC culture population that express the tested marker. Percentage of cells expressing the tested marker after growth in standard iMAC cell culture medium (white bars). Percentage of cells expressing the tested marker after growth in differentiation medium (black bars).

Passage 17 iMACs were also cultured in cardiomyocyte differentiation medium (DMEM/F12+10% FBS+10 uM 5-Azacytidine) for seven days and then evaluated by flow cytometry for the expression of isL1 and sarcomeric alpha actin (SA). Data showed that greater than 80% of iMACs up-regulate isL1. In contrast, 100% of iMACs express SA before and after treatment with cardiomyocyte differentiation medium (FIG. 9).

These data demonstrate that iMACs can differentiate into endothelial cells as well as cardiomyocytes. Therefore these cells may have utility in cardiovascular tissue engineering applications.

EXAMPLE 12

Human Internal Mammary Artery-Derived Cell Osteogenic Differentiation

For osteogenic differentiation, fresh passage 7 iMACs, isolated as described in Example 2, were plated at 5000 cells/cm$^2$ onto uncoated 12 well plates and cultured in iMAC Growth Medium at 37° C. in 5% carbon dioxide. When the cells reached near-confluence, iMAC Growth Medium was replaced with osteogenic induction medium (10-8 M dexamethasone, Sigma; 0.2 mM ascorbic acid, Sigma; and 10 mM betaglycerolphosphase, Sigma) and further cultured for 21 days, with media exchange every 2-4 days. To determine the extent of osteogenic differentiation, cells were fixed with 70% ice-cold ethanol for 1 hour. Cultures were rinsed with water and stained for 10 minutes with 1 mL of 40 mM Alizarin red (pH 4.1; Sigma) with rotation. Cultures were rinsed with PBS to reduce non-specific staining Stained cultured were then imaged on Day 5, 10 and 21 post induction. Human mesenchymal stem cells hMSC) (Lonza) were utilized as a positive control.

After 21 days of exposure to osteogenic induction medium, iMACs showed no mineral deposition and therefore no capacity for osteogenic differentiation. However, hMSCs showed robust mineral deposition.

EXAMPLE 13

Human Internal Mammary Artery-Derived Cell for Vascular Tissue Engineering

In an attempt to harness the unique anti-atherogenic and mechanical attributes of the internal mammary artery, we will isolate fresh iMACs and evaluate their utility in blood vessel and other cardiovascular tissue engineering applications.

iMACs will be seeded onto hollow tubular scaffolds composed of either natural or synthetic polymers, and cultured using a rotating wall vessel (RWV) bioreactor (Synthecon, Inc.) or a perfusion bioreactor (Tissue Growth Technologies, Inc.). One end of the tubular scaffold will be closed using a micro aneurysm clip (Roboz Surgical Instrument Co., Inc.) and the lumen will be filled with cell suspension (2500 cells/cm$^2$). The other end will be closed with another clip and the graft containing the cell suspension will be placed in the RWV bioreactor for 24 hours to allow for initial seeding of cells onto the inner surface of the scaffold. Alternately, IMA cells will be seeded onto the outer surface of the graft by adding cells to the culture medium bathing the tubular scaffold. After the initial 24-hour seeding period, the clips will be removed and the graft cultured within the bioreactor for an additional 4-7 days. In other experiments, the seeded tubular scaffold will be cultured under physiological, pulsatile flow and pressure using a perfusion bioreactor (Tissue Growth Technologies, Inc.). After the culture period, cell seeded constructs will be evaluated for cell attachment, viability, proliferattion and phenotype using the methods described above as well as histological methods.

In addition, the anti-arthrosclerosis properties of iMACs will be demonstrated. iMACs and human aortic smooth muscle cells (control cell line) will be cultured in 12-well plates. At confluence, the cells will be switched to calcification medium (growth medium containing 2 mM inorganic phosphate) for up to 14 days. The medium will be replaced with fresh medium every 2 days. Alternately, iMACs will be cocultured with smooth muscle cells in calcification medium. Cells will then be decalcified with 0.6 N HCl for 24 h. The calcium content of HCl supernatants will be determined colorimetrically by the o-cresolphthalein complexone method (Calcium Kit; Sigma). After decalcification, the cells will be washed three times with phosphate-buffered saline and solubilized with 0.1 N NaOH, 0.1% sodium dodecyl sulfate (SDS). The protein content will be measured with a BCA protein assay kit (Pierce, Rockford, Ill.). The calcium content of the cell layer will be normalized to protein content. Tissue engineered vascular grafts, utilizing iMACs, may be more resistant to atherosclerosis. IMACs may also provide for improved graft elasticity. Although the internal mammary artery has been utilized successfully for bypass grafting, it is susceptible to damage during surgical dissection. This undoubtedly will result in graft failure. Tissue engineered vascular grafts, composed of iMACs, may prove to be a superior alternative to traditional vascular grafting materials.

EXAMPLE 14

50/50 poly(p-dioxanone-co-glycolide) PDO/PLGA electrostatically spun tubular scaffolds were pre-wet with ethanol, coated for 1 hour at room temperature in 0.02N acetic acid with rat tail type I collagen (BD Biosciences, Bedford Mass.) following the manufacturer's instructions, and rinsed with phosphate buffered saline (PBS). iMAC cells isolated as described in Example 2 were then statically seeded onto the outside of collagen-coated tubes at a concentration of $4 \times 10^6$ cells/ml by pipetting 25 ul of cell suspension slowly onto each side of the tube, and incubating for 30 minutes at room temperature. The seeded tubes were then sutured onto bioreactor chamber barbs (Tissue Growth Technologies, Minnetonka, Minn.) and the chambers are filled with iMAC growth media. The inner lumen was seeded by adding iMAC cell suspension at $1 \times 10^6$ cells/ml using syringes. The seeded tubes within the bioreactor chambers are then cultured in a rotational manner at 0.5 rpm on a cell culture bottle-roller placed inside a 37° C. cell culture incubator. After 5 and 10 days of culture, the tubes were removed from the bioreactor chambers, fixed with 10% formalin and stained for histological analysis using hematoxylin and eosin (H&E).

Figure 10:
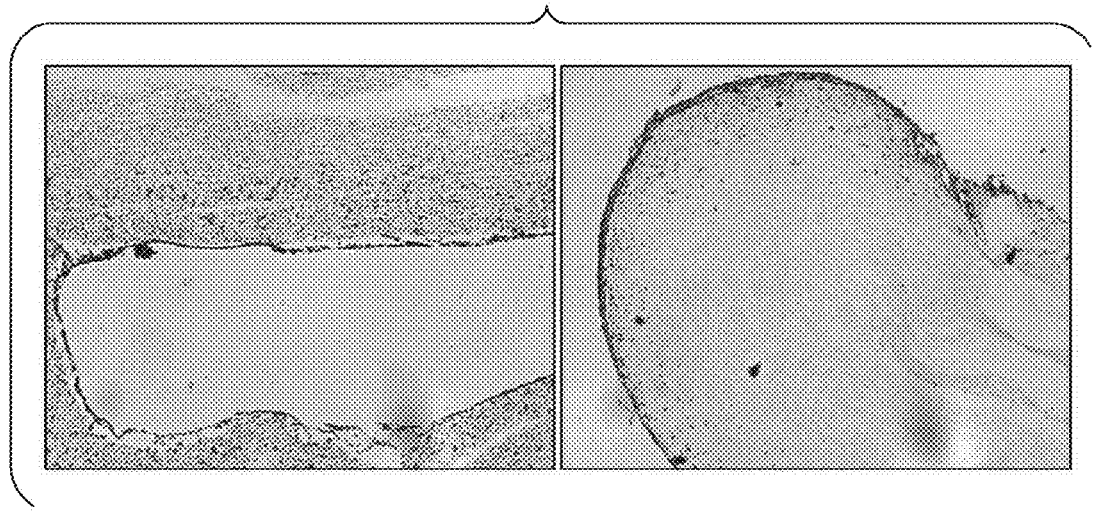
FIG. 10: Histology of iMAC-seeded tubular scaffolds. Tubular scaffolds were seeded both on the inner and outer surface with iMAC cells and cultured in a bioreactor chamber for 10 days. At this time, the scaffolds were fixed with formalin and stained with hematoxylin and eosin.

Histology results revealed that the iMAC cells attached and proliferated well on the electrostatically spun tubular scaffolds with some integration into the scaffold spaces. FIG. 10 shows histological cross-sections of the cell-seeded tubes indicating attachment and growth of the cells into multiple layers on both the inside and the outside of the tube surfaces. Cells can also be observed migrating into the inner layers of the electrostatically spun tubular scaffolds.

EXAMPLE 15

Electrostatically spun PCL scaffolds were prepared in the following manner. Solutions of 150 mg/mL of PCL (Lakeshore Biomaterials) in 1,1,1,3,3,3-hexafluoro-2-propanol (HFP, TCI America Inc.) solvent were prepared and left in a dark environment overnight on a shaker plate to ensure that all PCL had dissolved and formed a homogenous solution. The polymer solution (3 ml) was then drawn into a plastic Beckton Dickinson syringe (3 ml) and placed in a KD Scientific syringe pump (Model 100) to be dispensed at a rate of 5.5 ml/hr. A high voltage power supply (Spellman CZE1000R; Spellman High Voltage Electronics Corporation) was used to apply a voltage of +22 kV to a blunt tip 18 gauge needle fixed to the solution containing syringe. Solutions were electrospun onto a 2 mm diameter cylindrical grounded mandrel placed 8 inches from the needle tip and rotating at a rate of ~400 rpm to produce a scaffold of randomly oriented fibers. Mandrel translation distance was 18 cm, with a translational speed of 18 cm/s. Prior to electrospinning, the mandrel was wrapped with a small section of aluminum foil to aid in tube removal. Upon completion of electrospinning, the mandrel was immersed in 100% ethanol, and the foil liner was slid off the mandrel, and carefully removed from the inside of the tube.

Sterilized PCL electrostatically spun tubular scaffolds were pre-wet with 100% ethanol, washed with 0.02N acetic acid and coated with type 1 rat tail collagen (BD Biosciences, Bedford, Mass.) for one hour following manufacturer's instructions. The grafts were then washed twice with iMAC growth medium and sutured onto barbs of a bioreactor chamber (Tissue Growth Technologies, Minnetinka, Minn.). The outer chamber was filled with iMAC media and cell suspension at $1.2 \times 10^6$ cells/ml was used to seed the inner surface of the grafts. Syringes were used to fill the inner chamber with cell suspension, which was then capped and placed onto a cell culture bottle-roller placed inside a 37° C. cell culture incubator overnight. The next day the media in the inner chamber was exchanged with fresh media and to remove any unattached cells. The media in the inner chamber was again changed the next day. On the third day after seeding, the tubes were cut off the bioreactor chamber barbs, washed twice with 10 ml of serum-free Advanced DMEM/F12 medium and transferred to 5 ml cryovials for shipment. One sample was analyzed with Live/Dead stain (Invitrogen, Carlsbad, Calif.) following manufacturer's protocol. The sample was cut in half and one half was analyzed after a 3 hour room temperature mock ship, and the other half was analyzed after the same mock ship and an additional overnight incubation at 37° C. in a cell culture incubator in a 5 ml cryovial.

Figure 11:
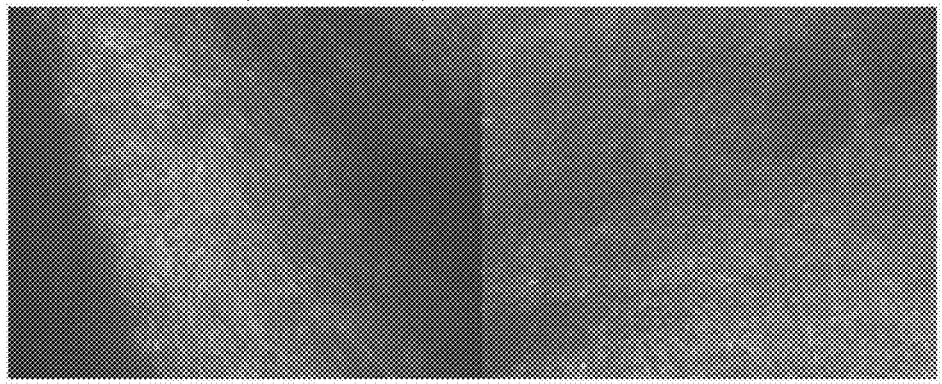
FIG. 11: Live/Dead staining of electrostatically spun PCL scaffolds seeded with iMAC cells. Electrostatically spun tubular PCL scaffolds were seeded with iMAC cells and cultured in a bioreactor chamber for 3 days. The cells were mock-shipped by incubating at room temperature for 3 hours, then returned to a standard cell culture incubator. At indicated times, pieces of the scaffold were cut off and stained with Live/Dead stain.
Figure 11:
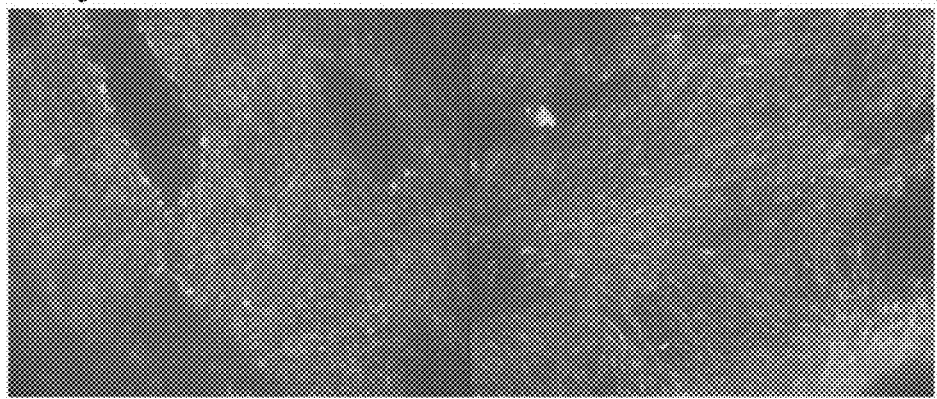

The remaining samples were implanted into the aortic artery of Lewis rats. Briefly, a segment of the infra-renal aortic artery was surgically removed and replaced with the cell-seeded tubular scaffold. The rats were then monitored for 4 weeks. The patency of the grafts was then assessed by CT angiography, and the graft inner diameter was periodically measured by ultrasound imaging. Four weeks after implantation, the animals were euthanized, the grafts excised and examined by histological staining FIG. 11 shows the Live/Dead assay results, indicating that iMACs attached and proliferated well on the PCL electrospun tube grafts, and remained viable after 3 days of culture, a 3 hour room temperature mock-ship, and an additional overnight incubation at 37° C. in a cell culture incubator. Very few dead cells were evident, the Live cells did not show any morphology changed indicative of stressed or dying cells.

Ultrasound measurement of the diameter of the iMAC-seeded scaffolds that were implanted into the aortic artery of Lewis rats show that the grafts remained patent up to 4 weeks after implantation, with minimal change in inner diameter. Results from CT angiography also indicated that the grafts remained patent. Histological staining with hematocylin and eosin after excision of the grafts at the 4 week timepoint showed no evidence of thrombosis formation and showed evidence of cellular integration into the scaffold. These results suggest that iMAC cells may be useful for repair and regeneration of damage to vascular tissues.

EXAMPLE 16

Human Internal Mammary Artery-Derived Cells Reproducibly Isolated from a Second Donor iMACs were isolated from a freshly obtained mammary artery derived from an new human donor using the method described in Example 2. Flow cytometry analysis was performed on this new lot of IMACs. Cells were expanded to passage eight in iMAC Growth Medium on type I rat tail collagen coated T75 flasks at 37° C. and 5% carbon dioxide. Adherent cells were washed in PBS and detached with TypleLE. Cells were harvested, centrifuged and resuspended in 3% (v/v) FBS in PBS at a concentration of $5 \times 10^5$ cells/mL. The specific antibody was added to 100 microliters of cell suspension and the mixture was incubated in the dark for 30-60 minutes at 4° C. After incubation, cells were washed twice with PBS and centrifuged to remove excess antibody. Cells were resuspended in 300 microliters PBS and analyzed by flow cytometry. Flow cytometry analysis was performed with a Guava instrument. Antibodies used are shown in Table 10.

TABLE 10

Antibodies used to characterize the iMAC cell surface marker phenotype.

| Antibody | Manufacture | Catalog number |
|---|---|---|
| CD10 | BD Pharmingen | 555375 |
| CD15 | BD Pharmingen | 555401 |
| CD23 | BD Pharmingen | 555711 |
| CD24 | BD Pharmingen | 555428 |
| CD29 | BD Pharmingen | 555442 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD49C | BD Pharmingen | 556025 |
| CD62P | BD Pharmingen | 555523 |
| CD73 | BD Pharmingen | 550257 |
| CD80 | BD Pharmingen | 557226 |
| CD86 | BD Pharmingen | 555657 |
| CD104 | BD Pharmingen | 555720 |
| CD133 | Miltenyi Biotech | 130090853 |
| CD138 | BD Pharmingen | 550805 |
| CD141 | BD Pharmingen | 559781 |
| CD142 | BD Pharmingen | 550312 |
| CD146 | BD Pharmingen | 561013 |
| CD166 | BD Pharmingen | 559263 |
| HLA-I | BD Pharmingen | 555553 |
| HLA-II | BD Pharmingen | 555558 |
| IgG-FITC | BD Pharmingen | 555748 |
| IgG-PE | BD Pharmingen | 555749 |

Passage 8 cultures of iMACs showed positive staining for CD29, CD44, CD73, CD 166 and HLA-1. iMACs showed negative staining for CD10, CD15, CD23, CD24, CD31, CD34, CD45RA, CD62p, CD80, CD86, CD104, CD133, CD138, CD141, CD146 and HLAII.

Results (Table 11) demonstrate that iMACs can be isolated from human internal mammary arteries obtained from different donors and still maintain a consistent and reproducible phenotype. iMACs described in Example 2 were derived from a 51 year old female, whereas iMACs described in this Example were isolated from a 56 year old male. It is evident that although iMACs express some markers in common with mesenchymal stem cells, CD10 is not expressed by iMACs. In addition, the smooth muscle cell marker CD141 is not expressed by iMACs. iMACs do not express markers that are typically expressed by endothelial cells, nor hematopoietic cells. These data are consistent with our previous findings described in Example 7.

Further evaluation is necessary to characterize the growth properties and differentiation potential of this donor. However based on these results, it is expected that these cellular characteristics will remain constant with past findings. Data described here suggests that iMACs can be reproducibly isolated from different human internal mammary arteries. This enhances the potential for using iMACs in widespread clinical applications.

TABLE 11

Cell surface marker phenotype. iMACs were characterized by flow cytometry using the antibodies described in Table 10. Markers were organized according to known surface markers of specific cell types (Cell type). Surface markers expressed by the specific cell type (Cell-type expression). iMACs that express tested surface marker (Positive). Positive staining was determined by comparing test antibody staining profile to negative control antibody staining. Staining of greater than 75% of cells was considered positive. iMACs that do not express tested surface marker (Negative) Staining was considered negative if less than 25% cells were positive compared to a negative control antibody.

| Cell type | Antibody | Cell-type expression | iMAC expression |
|---|---|---|---|
| Endothelial progenitor cells | CD34 | Positive | Negative |
| | CD133 | Positive | Negative |
| | CD45 RA | Positive | Negative |
| Endothelial cells | CD31 | Positive | Negative |
| | CD104 | Positive | Negative |
| Smooth muscle cells | CD141 | Positive | Negative |
| Mesenchymal stem cells | CD10 | Positive | Negative |
| | CD29 | Positive | Positive |
| | CD44 | Positive | Positive |
| | CD73 | Positive | Positive |
| | CD166 | Positive | Positive |
| Other | CD15 | Positive | Negative |
| | CD23 | Positive | Negative |
| | CD24 | Positive | Negative |
| | CD62p | Positive | Negative |
| | CD80 | Positive | Negative |
| | CD86 | Positive | Negative |

TABLE 11-continued

Cell surface marker phenotype. iMACs were characterized by flow cytometry using the antibodies described in Table 10. Markers were organized according to known surface markers of specific cell types (Cell type). Surface markers expressed by the specific cell type (Cell-type expression). iMACs that express tested surface marker (Positive). Positive staining was determined by comparing test antibody staining profile to negative control antibody staining. Staining of greater than 75% of cells was considered positive. iMACs that do not express tested surface marker (Negative) Staining was considered negative if less than 25% cells were positive compared to a negative control antibody.

| Cell type | Antibody | Cell-type expression | iMAC expression |
|---|---|---|---|
| | CD138 | Positive | Negative |
| | CD146 | Positive | Negative |
| | HLA 1 | Positive | Positive |
| | HLA 2 | Positive | Negative |

EXAMPLE 17

Isolation of Human Internal Mammary Artery-Derived Cells from a Third Donor

The optimal digestion time interval (described in Example 1) was then applied to isolate internal mammary artery-derived cells. A ten centimeter portion of the human internal mammary artery was obtained from the National Disease Research Interchange (NDRI, Philadelphia, Pa.). The artery was cleaned of surrounding fat and tissue and washed in iMAC Growth Medium (Advanced DMEM/F12 (Gibco), L-glutamine (Gibco), penicillin (50 Units/milliliter) and streptomycin (50 ug/mL, Gibco)) containing 10% fetal bovine serum (Hyclone)) and phosphate buffered saline (PBS; Invitrogen, Carlsbad, Calif.) to remove blood and debris. The entire artery was then transferred to a 50-milliliter conical tube.

The tissue was then digested in an enzyme mixture containing 0.25 Units/milliliter collagenase (Serva Electrophoresis, Heidelberg, Germany) and 2.0 Units/milliliter dispase (Roche Diagnostics Corporation, Indianapolis Ind.). The enzyme mixture was then combined with Advanced DMEM/F12 (Gibco). The conical tube containing the tissue, Advanced DMEM/F12, and digestion enzymes was incubated at 37° C. in an orbital shaker at 250 rpm for 1 hour. The partially digested artery was then transferred to a 50 mL conical tube containing a mixture of fresh enzymes and Advanced DMEM/F12 and further digested at 37° C. for 1 hour. The digested artery was then removed from the 50 mL conical tube and discarded. The resulting digest was then centrifuged at 150×g for 5 minutes, the supernatant was aspirated. The pellet was washed by resuspending in iMAC Growth Medium (total volume 25 milliliters) and centrifuged at 150×g for 5 minutes. The supernatant was aspirated and the cells were resuspended in 2 milliliters of fresh iMAC Growth Medium and plated into a tissue culture flask that was coated with 30 ug/cm² bovine type I collagen (Sigma-Aldrich, St Louis Mo.). The cells were then cultured at 37° C. and 5% $CO_2$. Cells were cultured for 6-7 passages and then cryopreserved at $1-2e^6$ cells/mL of cryoprotectant solution (Advanced DMEM/F12, 10% FBS) using standard cryopreservation methods.

Human Internal Mammary Artery-Derived Cell Surface Marker Phenotype

Flow cytometry analysis was performed on iMACs isolated as described above at two different timepoints. Cells were expanded to passage nine and twenty-one in growth medium on type I collagen coated T75 flasks at 37° C. and 5% carbon dioxide. Adherent cells were washed in PBS and detached with TypleLE (Gibco). At each time-point, cells were harvested, centrifuged and resuspended in 3% (v/v) FBS in PBS at a concentration of $5 \times 10^5$ cells/mL. Each specific antibody was added to 100 microliters of cell suspension and the mixture was incubated in the dark for 60 minutes at 4° C. After incubation, cells were washed twice with PBS and centrifuged to remove excess antibody. Cells were resuspended in 300 microliters PBS and analyzed by flow cytometry. Flow cytometry analysis was performed with a Guava EasyCyte instrument. Antibodies used are shown in Table 12.

Surface marker expression results are shown in Table 13. Positive staining was determined by comparing test antibody staining profile to the appropriate negative control antibody staining. Staining of greater than 75% of cells was considered positive. Staining was considered negative if less than 25% cells were positive compared to the negative control antibody. Passage nine and twenty-one cultures of iMACs showed positive staining for CD13, CD29, CD44, CD49c, CD73, CD90, CD105, CD140a, CD140b, CD166 and HLA-1 and negative staining for CD10, CD15, CD23, CD24, CD31, CD34, CD45RA, CD56, CD62p, CD80, CD86, CD104, CD117, CD133, CD138, CD141, CD144, CD146, CD309, and HLA-2.

TABLE 12

Antibodies used in characterization of iMAC cell surface marker expression.

| Antibody | Manufacturer | Catalog number |
|---|---|---|
| IgG-PE | BD Pharmingen | 340761 |
| IgG-FITC | BD Pharmingen | 340755 |
| CD10 | BD Pharmingen | 555375 |
| CD13 | BD Pharmingen | 347837 |
| CD15 | BD Pharmingen | 555401 |
| CD23 | BD Pharmingen | 555711 |
| CD24 | BD Pharmingen | 555428 |
| CD29 | BD Pharmingen | 555443 |
| CD31 | BD Pharmingen | 555446 |
| CD34 | BD Pharmingen | 555478 |
| CD44 | BD Pharmingen | 555821 |
| CD45RA | BD Pharmingen | 555489 |
| CD49c | BD Pharmingen | 556025 |
| CD56 | BD Pharmingen | 555516 |
| CD62p | BD Pharmingen | 555523 |
| CD73 | BD Pharmingen | 550257 |
| CD80 | BD Pharmingen | 557226 |
| CD86 | BD Pharmingen | 555657 |
| CD90 | BD Pharmingen | 555595 |
| CD 104 | BD Pharmingen | 555720 |
| CD 105 | BD Pharmingen | 560839 |
| CD117 | BD Pharmingen | 555714 |
| CD133 | Miltenyi Biotech | 130-090-853 |
| CD138 | BD Pharmingen | 550805 |
| CD140a | BD Pharmingen | 556002 |
| CD140b | BD Pharmingen | 558821 |
| CD141 | BD Pharmingen | 559781 |
| CD 144 | BD Pharmingen | 560411 |
| CD 146 | BD Pharmingen | 561013 |
| CD 166 | BD Pharmingen | 559263 |
| CD309 | BD Pharmingen | 560494 |
| HLA-1 | BD Pharmingen | 555553 |
| HLA-2 | BD Pharmingen | 555558 |

Results and Discussion of CD105 Difference Between Example 2 and 17

Comparison of surface marker expression data between the lot of cells isolated in Example 2 and the cells isolated in Example 17 revealed an inconsistency in a single surface marker—CD105. The major difference between these two experiments with regard to this surface marker was the supplier of the antibody used for the analysis. The analysis of surface marker expression in Example 2 used an anti-CD105 antibody from Santa Cruz Biotechnology Inc., whereas the surface marker expression analysis in Example 17 used an anti-CD105 antibody from BD Pharmingen.

TABLE 13 iMAC cell surface marker phenotype.
iMACs were characterized by flow cytometry using the antibodies described in Table 12. iMACs that express tested surface marker (Positive). Positive staining was determined by comparing test antibody staining profile to the appropriate negative control antibody staining. Staining of greater than 75% of cells was considered positive. iMACs that do not express tested surface marker (Negative). Staining was considered negative if less than 25% cells were positive compared to a negative control antibody.

| Marker | passage 9 | passage 21 |
| --- | --- | --- |
| CD10 | Negative | Negative |
| CD13 | Positive | Positive |
| CD15 | Negative | Negative |
| CD23 | Negative | Negative |
| CD24 | Negative | Negative |
| CD29 | Positive | Positive |
| CD31 | Negative | Negative |
| CD34 | Negative | Negative |
| CD44 | Positive | Positive |
| CD45RA | Negative | Negative |
| CD49c | Positive | Positive |
| CD56 | Negative | Negative |
| CD62p | Negative | Negative |
| CD73 | Positive | Positive |
| CD80 | Negative | Negative |
| CD86 | Negative | Negative |
| CD90 | Positive | Positive |
| CD 104 | Negative | Negative |
| CD 105 | Positive | Positive |
| CD117 | Negative | Negative |
| CD133 | Negative | Negative |
| CD138 | Negative | Negative |
| CD140a | Positive | Positive |
| CD140b | Positive | Positive |
| CD141 | Negative | Negative |
| CD 144 | Negative | Negative |
| CD 146 | Negative | Negative |
| CD 166 | Positive | Positive |
| CD309 | Negative | Negative |
| HLA-1 | Positive | Positive |
| HLA-2 | Negative | Negative |

What is claimed:

1. An in vitro cell culture comprising:
a culture vessel;
a culture medium comprising internal mammary artery-derived cell growth medium; and
cells derived from a mammalian internal mammary artery and capable of self-renewal and expansion in culture,
wherein said cells are positive for the expression of cell-surface marker HLA-1 and negative for expression of each one of cell-surface markers CD 10, CD31, CD34, CD45, CD133, CD141 and KDR/Flk-1, and
wherein said cells are plated in the culture vessel with the culture medium.

2. The cell culture of claim 1, wherein the cells are capable of differentiation into adipocytes, cardiomyocytes, and endothelial cells.

3. The cell culture of claim 1 wherein the culture vessel is coated.

4. The cell culture of claim 3 wherein the culture vessel is coated with collagen.

5. The cell culture of claim 1 wherein the cells are additionally positive for expression of CD29, CD44, CD73, CD166, and additionally negative for CD15, CD23, CD24, CD62p, CD80, CD86, CD104, CD117, CD138, CD146, VE-Cadherin, and HLA-2.

* * * * *